US006661008B2

(12) United States Patent
Takagi et al.

(10) Patent No.: US 6,661,008 B2
(45) Date of Patent: *Dec. 9, 2003

(54) ELECTRON-OPTICAL SYSTEM AND INSPECTION METHOD USING THE SAME

(75) Inventors: Toru Takagi, Kawasaki (JP); Akihiro Goto, Tokyo (JP)

(73) Assignee: Nikon Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/337,131

(22) Filed: Jun. 21, 1999

(65) Prior Publication Data

US 2003/0025076 A1 Feb. 6, 2003

(30) Foreign Application Priority Data

| Jun. 22, 1998 | (JP) | 10-192486 |
| Jun. 22, 1998 | (JP) | 10-192487 |
| Aug. 21, 1998 | (JP) | 10-235108 |

(51) Int. Cl.$^7$ ............... H01J 49/0044; H01J 37/0026
(52) U.S. Cl. ............ 250/310; 250/305; 250/306; 250/311; 250/492.1; 250/492.2; 250/492.21; 250/596 R; 250/396 ML
(58) Field of Search .............. 250/310, 492.1, 250/492.2, 492.22, 492.23, 305, 306, 311

(56) References Cited

U.S. PATENT DOCUMENTS

| 4,812,651 | A | * | 3/1989 | Feuerbaum et al. | 250/310 |
| 4,978,855 | A | * | 12/1990 | Liebl et al. | 250/310 |
| 5,116,118 | A | * | 5/1992 | Jones | 5/92 |
| 5,389,787 | A | | 2/1995 | Todokoro et al. | 250/310 |
| 5,424,541 | A | | 6/1995 | Todokoro et al. | 250/310 |
| 5,502,306 | A | * | 3/1996 | Meisburger et al. | 250/310 |
| 5,614,833 | A | * | 3/1997 | Golladay | 324/751 |
| 6,184,526 | B1 | * | 2/2001 | Kohama et al. | 250/310 |
| 6,259,094 | B1 | * | 7/2001 | Nagai et al. | 250/310 |
| 6,310,341 | B1 | * | 10/2001 | Todokoro et al. | 250/305 |

OTHER PUBLICATIONS

K. Tsuno, *Simulation of a Wien filter as beam separator in a low energy electron microscope*, Ultramicroscopy 55 (1994), pp. 127–140.

* cited by examiner

Primary Examiner—John R. Lee
Assistant Examiner—David A. Vanore
(74) Attorney, Agent, or Firm—Morgan, Lewis & Bockius LLP

(57) ABSTRACT

An electron-optical system, including irradiation means which irradiates a surface of a sample with an irradiating electron beam and observation means which focuses an observational electron beam emitted from the surface of the sample as an image on electron beam detection means. The observation means includes a plurality of electrodes. The electron-optical system further includes an accelerating electric field disposed between the surface of the sample and at least one of the plurality of electrodes so that the sample is biased to a negative potential, and so that the velocity of the observational electron beam that has just been emitted from the surface of the sample increases monotonically to a positive potential. The velocity of the observational electron beam that has been accelerated to the positive potential is reduced to the ground potential by another of the plurality of electrodes which form the observation means.

12 Claims, 14 Drawing Sheets

ELECTRON-OPTICAL SYSTEM AND INSPECTION METHOD USING THE SAME

FIELD OF THE INVENTION

The present invention concerns an electron-optical system for use in performing observations or inspections, etc., of sample surfaces by means of an electron beam, and an inspection method using the same.

BACKGROUND OF THE INVENTION

Electron microscopes using electron beams have been widely used in the past for the observation and inspection of miniaturized, highly integrated semiconductor elements, etc. Electron microscopes include microscopes known as low-energy electron microscopes (K. Tsuno, Ultramicroscopy 55 (1994) 127–140 "Simulation of a Wien filter as a beam separator in a low energy electron microscope").

A low-energy electron microscope will be briefly described with reference to FIG. 3. An electron beam (irradiating electron beam S) which is accelerated to approximately 10 keV by an electron gun 1 is shaped by illumination lenses 2 and 3, and is then directed onto a beam separator 4. The electron beam deflected by the beam separator 4 passes through an aperture diaphragm 5, and then irradiates a sample 7 after passing through a cathode lens 6.

Here, the cathode lens 6 consists of three electrodes 6a, 6b and 6c installed along to the direction of the optical axis, and is an electron lens, i. e., a so-called einzel lens, in which the center electrode 6b of the above-mentioned electrodes is biased to a negative potential, and the electrodes 6a and 6c on both ends are grounded. The potential of this central electrode 6b is a high potential of approximately −7 to −10 kV.

Meanwhile, the sample 7 is biased to a high voltage of approximately −10 kV, so that an electric field is formed between the sample 7 and the first electrode 6a of the cathode lens 6 which is positioned closest to the sample 7. The irradiating electron beam S reaches the sample 7 after being decelerated to approximately 10 eV by this electric field.

When the sample 7 is irradiated by the electron beam, secondary electrons, reflected electrons and back-scattered electrons, etc., are emitted from the sample. Electrons of at least one of these types constitute an observational electron beam K. Here, the velocity of the reflected electrons is approximately 10 eV.

The observational electron beam K that is emitted from the sample 7 is again accelerated to approximately 10 keV by the electric field formed between the sample 7 and the first electrode 6a of the cathode lens 6. Afterward, the observational electron beam K passes through the other electrodes 6b and 6c of the cathode lens 6, and then enters the beam separator 4 after further passing through the aperture diaphragm 5. Then, the observational electron beam K, which passes through the beam separator 4 in a straight line as a result of the Wien condition being satisfied, is focused as an image on an electron beam detector 11 such as an MCP (micro-channel plate), etc., after passing through image-focusing lenses 8 and 10.

Here, like the cathode lens 6, the illumination lenses 2 and 3 and image-focusing lenses 8 and 10 are einzel lenses, and the central electrodes of these lenses are biased to a high potential of approximately −5 to −10 kV.

The above-mentioned conventional electron-optical system possesses the following advantage: specifically, since the energy of the electron beam is high when the electron beam passes through the illumination lenses, cathode lens and image-focusing lenses, the chromatic aberration is low. However, the following two major problems have been encountered:

The first problem is that the cost of the electron-optical system is extremely high. Specifically, as was described above, the einzel lenses constituting the illumination lenses, cathode lens and image-focusing lenses all require the application of a high voltage. As a result, extremely expensive high-voltage power supplies and electrodes with a high withstand voltage are used.

Here, in cases where a relatively low voltage is applied to the respective einzel lenses instead of a high voltage being applied, i. e., in cases where a low-cost power supply and electrodes are used, the focal lengths of the respective einzel lenses are increased, so that the overall length of the electron path is increased by a corresponding amount. Thus, since the size of the electron-optical system is increased, it is difficult to reduce the cost of the einzel lenses.

The other problem is that a long time is required for the elevation of the voltage that accompanies the application of a high voltage to the sample. In other words, the observational efficiency is low. As was described above, a high voltage is applied to the sample; however, if a high voltage is abruptly applied, the sample will be damaged, and this damage may lead to failure in some cases. Accordingly, the elevation of the voltage applied to the sample is accomplished over a period of time in order to avoid damaging the sample.

These problems are even more severe in cases where secondary electrons are used for the observational electron beam than they are in cases where reflected electrons are used for the observational electron beam. The reason for this is as follows: generally, while reflected electrons are emitted from the sample in one direction, secondary electrons are emitted from the sample in an isotropic manner. Accordingly, in the case of secondary electrons, it is necessary to increase the quantity of secondary electrons drawn from the sample toward the cathode lens, i. e., the so-called yield, in order to improve the precision (S/N) of observation. Consequently, the electric field formed between the sample and the first electrode of the cathode lens must be correspondingly strengthened. As a result, a high voltage must be applied to the sample and to the illumination lenses, cathode lens and image-focusing lenses consisting of einzel lenses, thus fostering the two problems mentioned above.

Here, in cases where a method in which the yield of secondary electrons is increased by increasing the internal diameter of the aperture diaphragm is adopted in order to improve the precision of observation by means of secondary electrons, instead of adopting a method in which the electric field between the sample and the first electrode is strengthened as described above, a separate problem arises in place of the above-mentioned problems: namely, the aberration becomes worse, so that the resolution drops.

SUMMARY OF THE INVENTION

Accordingly, the object of the present invention is to provide an electron-optical system which has a low cost and a high observational efficiency while maintaining the overall electron path length and quality of observation, such as yield of observational electrons and resolution, etc.

The present invention was devised in order to achieve the above-mentioned object. Specifically, with symbols appearing in the attached figures noted in parentheses, the present invention is an electron-optical system which is characterized by the fact that in an electron-optical system which is equipped with an irradiation means that irradiates the surface of a sample (7) with an irradiating electron beam (S), and an observation means that focuses an observational electron beam (K) emitted from the surface of the sample (7) as an image on an electron beam detection means (11), and in which potential difference that accelerates the observational electron beam (K) is created between the surface of the sample (7) and the electrode (6a) of the observation means that is positioned closest to the surface of the sample (7), the electrode (6a) of the observation means that is positioned closest to the surface of the sample (7) is biased to a positive potential with respect to the ground potential.

Furthermore, the present invention is an electron-optical system which is characterized by the fact that in an electron-optical system in which an irradiating electron beam (S) generated from an irradiating beam source (1) is caused to be incident on the beam separator (4) via an illumination optical system (2, 3), the irradiating electron beam (S) passing through the beam separator (4) is caused to be incident on the surface of the sample (7) via an objective optical system (6), an observational electron beam (K) emitted from the surface of the sample (7) is caused to be incident on the beam separator (4) via the objective optical system (6), the observational electron beam (K) is directed by the beam separator (4) in a direction that differs from the direction leading to the irradiating beam source (1), the observational electron beam (K) that has passed through the beam separator (4) is caused to be incident on an electron beam detection means (11) via an image-focusing optical system (8, 10), and a potential difference that accelerates the observational electron beam (K) is created between the surface of the sample (7) and the electrode (6a) of the objective optical system (6) that is positioned closest to the surface of the sample (7), the electrode (6a) of the objective optical system (6) that is positioned closest to the surface of the sample (7) is biased to a positive potential with respect to the ground potential.

DETAILED DESCRIPTION OF THE PREFERRED EMBODIMENTS (First Embodiment)

Figure 1:
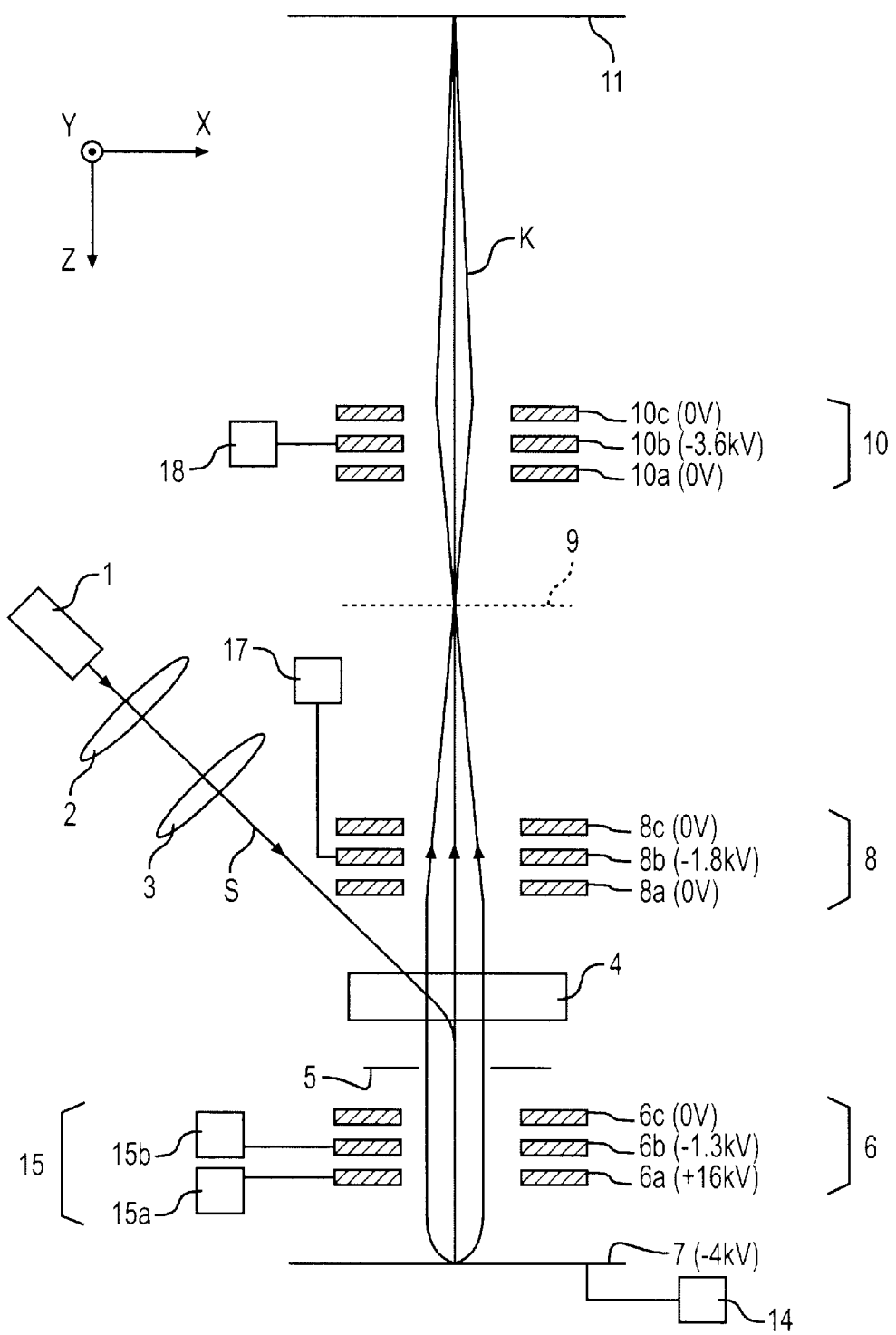
FIG. 1 is a diagram which illustrates an electron-optical system constructed according to a first embodiment of the present invention.

A working configuration of the present invention will be described with reference to the attached figures. FIG. 1 illustrates a first embodiment of the electron-optical system of the present invention. An irradiating electron beam S emitted from an electron gun 1 is shaped by illumination lenses 2 and 3, and then enters a beam separator 4. Here, the irradiating electron beam S is accelerated to 5 keV. Furthermore, the illumination lenses 2 and 3 are einzel lenses which consist of three electrodes (not shown in the figures). Furthermore, for example, a Wien filter is used as the beam separator 4.

The irradiating electron beam S which enters the beam separator 4 and is deflected forms a cross-over image at the position of an aperture diaphragm 5, and then passes through a cathode lens 6 so that this beam S illuminates the sample 7 with Koehler illumination.

Here, the cathode lens 6 is constructed from three electrodes, i. e., a first cathode lens electrode 6a, a second cathode lens electrode 6b and a third cathode lens electrode 6c. Furthermore, the first cathode lens electrode 6a is biased to +16 kV by a first electrode power supply 15a. The second cathode lens electrode 6b is biased to −1.3 kV by a second electrode power supply 15b. The third cathode lens electrode 6c is grounded. Thus, the cathode lens 6 has a structure which differs from that of an einzel lens in which the electrodes at both ends are grounded.

Furthermore, the sample 7 is biased to −4 kV by a sample power supply 14. Thus, an electric field (hereafter referred to as the "first electric field") is formed between the sample 7 and the first cathode lens electrode 6a. The irradiating electron beam S reaches the sample 7 after being decelerated to 1 keV by this first electric field. Here, the electron gun 1, illumination lenses 2 and 3, beam separator 4, aperture diaphragm 5 and cathode lens 6 constitute an irradiation means.

Secondary electrons with an energy of approximately 1 to 2 eV are emitted from the sample 7; these electrons are used as an observational electron beam K. When this observational electron beam K is drawn upward by the first electric field and caused to pass through the first cathode lens electrode 6a, the beam K is accelerated to approximately 20 keV. The observational electron beam K which has passed through the first cathode lens electrode 6a is decelerated to 4 keV after passing through the second cathode lens electrode 6b and third cathode lens electrode 6c.

The observational electron beam K which has passed through the cathode lens 6 passes through the aperture diaphragm 5, and enters the beam separator 4. The observational electron beam K, which passes through the beam separator 4 in a straight line as a result of the Wien condition being satisfied, passes through an image-focusing lens front group 8, and then tentatively forms an intermediate image of the sample 7 at an intermediate-image focusing position 9. Here, the image-focusing lens front group 8 is an einzel lens, and is constructed from three electrodes, i. e., an image-focusing lens front-group first electrode 8a, an image-focusing lens front-group second electrode 8b, and an image-focusing lens front-group third electrode 8c. Furthermore, the image-focusing lens front-group first electrode 8a and image-focusing lens front-group third electrode 8c, which are the electrodes at both ends, are grounded, while the image-focusing lens front-group second electrode 8b, which is the central electrode, is biased to −1.8 kV.

Furthermore, the observational electron beam K that has passed through the intermediate-image focusing position 9 passes through an image-focusing lens rear group 10, and then forms an enlarged projected image of the sample 7 on an electron beam detector 11. Here, the cathode lens 6, aperture diaphragm 5, beam separator 4, image-focusing lens front group 8 and image-focusing lens rear group 10 constitute the observation means.

Here, the image-focusing lens rear group 10, like the image-focusing lens front group 8, is an einzel lens, and is constructed from three electrodes, i. e., an image-focusing lens rear-group first electrode 10a, an image-focusing lens rear-group second electrode 10b, and an image-focusing lens rear-group third electrode 10c. Furthermore, the image-focusing lens rear-group first electrode 10a and image-focusing lens rear-group third electrode 10c are grounded, while the image-focusing lens rear-group second electrode 10b is biased to −3.6 kV.

Thus, in this first embodiment, the potential applied to the sample 7 can be reduced to a relatively low value; accordingly, the time required for elevation of the voltage can be shortened, so that the observational efficiency can be improved. Furthermore, in addition to the sample power supply 14, the potentials supplied from the power supply of the illumination lenses 2 and 3, the image-focusing lens front-group power supply 17 and the image-focusing lens rear-group power supply 18 can also be reduced to relatively low values, so that the cost of the apparatus as a whole can be reduced.

Furthermore, since a positive potential is applied to the first electrode 6a of the cathode lens, a construction is obtained in which impurities consisting of positive ions tend not to adhere to this electrode.

Furthermore, in this first embodiment, an intermediate image is first formed by the optical system consisting of the cathode lens 6 and image-focusing lens front group 8, i. e., by a so-called two-sided telecentric optical system, and this intermediate image is enlarged and projected onto the surface of an electron beam detector 11 by the image-focusing lens rear group 10. However, it would also be possible to remove this image-focusing lens rear group 10, and to install the electron beam detector 11 at the intermediate-image focusing position 9.

Moreover, in this first embodiment, a case was described in which a two-sided telecentric optical system was constructed by the cathode lens 6 and image-focusing lens front group 8; however, it is not necessary to form a two-sided telecentric optical system.

Furthermore, in this first embodiment, secondary electrons were used as the observational electron beam K; however, it would also be possible to use reflected electrons or back-scattered electrons instead. In such cases, it is necessary merely to alter the voltages applied to the respective lenses.

Furthermore, it would also be possible to use ion beams with positive charges instead of the irradiating electron beam S and observational electron beam K used in the first embodiment. In such a case, the first cathode lens electrode 6a is negatively biased with respect to the ground potential.

Furthermore, in the first embodiment, an electrostatic type electron lens consisting of three electrodes was used as the cathode lens 6; however, since it is sufficient if a first electric field can be formed, it would also be possible to eliminate the second cathode lens electrode 6b and third cathode lens electrode 6c, and to use a construction consisting of the first cathode lens electrode 6a and a magnetic field type lens.

Next, simulated results obtained for resolution and magnification using the electron-optical system of the first embodiment are shown in Table 1. For the sake of simplicity, the simulation was performed for the resolution and magnification of the cathode lens 6 and image-focusing lens front group 8 at the intermediate-image focusing position 9. The actual simulation was performed using a two-dimensional finite element method. Specifically, the electrostatic fields in the cathode lens 6 and image-focusing lens front group 8 were respectively determined, and the track of the electron beam was determined by numerically solving equations of motion for these electrostatic fields.

Furthermore, in order to confirm the effect of the first embodiment, a comparison was made with a conventional technique using an einzel lens as the cathode lens 6. In regard to the voltages applied to the respective lenses in the conventional technique, the potentials required in order to obtain a resolution comparable to that of the first embodiment were estimated.

TABLE 1

| | | First Embodiment | Conventional Technique |
|---|---|---|---|
| Applied Voltage | Sample | −4 kV | −20 kV |
| | First cathode lens electrode | +16 kV | 0 V |
| | Second cathode lens electrode | −1.3 kV | −15 kV |
| | Third cathode lens electrode | 0 V | 0 V |
| | First electrode of image-focusing lens front group | 0 V | 0 V |
| | Second electrode of image-focusing lens front group | −1.8 kV | −10 kV |
| | Third electrode of image-focusing lens front group | 0 V | 0 V |
| Results of Simulation | In-axis resolution | 0.2 μm | 0.2 μm |
| | Out-of-axis resolution | 0.5 μm | 0.5 μm |
| | Enlargement magnification | 3.2 times | 1.3 times |

Furthermore, the above-mentioned simulation was performed under the following conditions:

Visual field of observation: 200 μm × 200 μm
Secondary electron yield: 1% of secondary electrons generated from sample -continued

| | |
|---|---|
| Secondary electron chromatic dispersion: | 1 eV |
| Total length: | 400 mm |

Furthermore, since the chromatic aberration is determined mostly by the intensity of the first electric field, the intensity of the first electric field was set at the same value in the first embodiment and in the conventional technique.

Here, the secondary electron chromatic dispersion indicates the energy dispersion of the secondary electrons constituting the observational electron beam K. Since electron beams of different energies follow different tracks, aberration is generated. This aberration is generally considered to be chromatic aberration in electron-optical systems. Furthermore, the total length indicates the distance between the sample 7 and the intermediate-image focusing position 9.

The following effects can be confirmed from the simulated results obtained for resolution and magnification in Table 1. First of all, in a case where it is attempted to obtain a comparable secondary electron yield and to achieve a comparable resolution by means of a cathode lens 6, a voltage of −4 kV can be applied to the sample 7 in the first embodiment, while it is necessary to apply a voltage of −20 kV in the conventional technique. In other words, the voltage rise time of the sample power supply 14 can be shortened.

Secondly, the voltage applied to the image-focusing lens front-group second electrode 8b can be greatly reduced. In other words, the cost of the image-focusing lens front-group power supply 17 can be reduced. Meanwhile, since the potential of the first cathode lens electrode 6a in the first embodiment and the potential of the second cathode lens electrode 6b in the conventional technique are roughly equal, the cost of the cathode lens power supply 15 of the first embodiment can be equivalent to a cost that is comparable to that of the cathode lens power supply 15 of the conventional technique. Here, it is necessary to apply a voltage of −1.3 kV to the second cathode lens electrode 6b in the first embodiment; however, there is no need to add a power supply not seen in the conventional technique for this purpose. Specifically, the potential of the second cathode lens electrode 6b is a low potential, and can be supplied via a resistance, etc., from a cathode lens power supply 15 that is shared with the first cathode lens electrode 6a. Accordingly, the cost of the cathode lens power supply 15 is roughly the same as that used in the conventional technique. Thus, the cost of the apparatus as a whole can be lowered.

Third, the enlargement magnification at the intermediate image position 9 is greater in the first embodiment than in the conventional technique. The reason for this is that in the first embodiment, the energy of the electron beam is lower than in the conventional technique, so that the refractive index following emission from the cathode lens 6 is lower. As a result, in cases where a two-sided telecentric optical system is constructed by the cathode lens 6 and image-focusing lens front group 8, the apparent back-side focal length is shortened, so that the enlargement magnification at the intermediate-image focusing position 9 is increased. Furthermore, the refractive index of an electron-optical system can generally be estimated as the square root of the electron energy.

Furthermore, the above-mentioned simulation was performed at the intermediate-image focusing position 9 created by the cathode lens 6 and image-focusing lens front group 8; however, similar results can be derived even if the image-focusing lens rear group 10 is included in this. Specifically, the voltage applied to the image-focusing lens rear group 10 can be reduced without causing any deterioration in the secondary electron yield or resolution, and without lengthening the distance between the sample 7 and the electron beam detector 11. Furthermore, similar results can also be derived for the illumination lenses 2 and 3.

(Second Embodiment)

Figure 2:
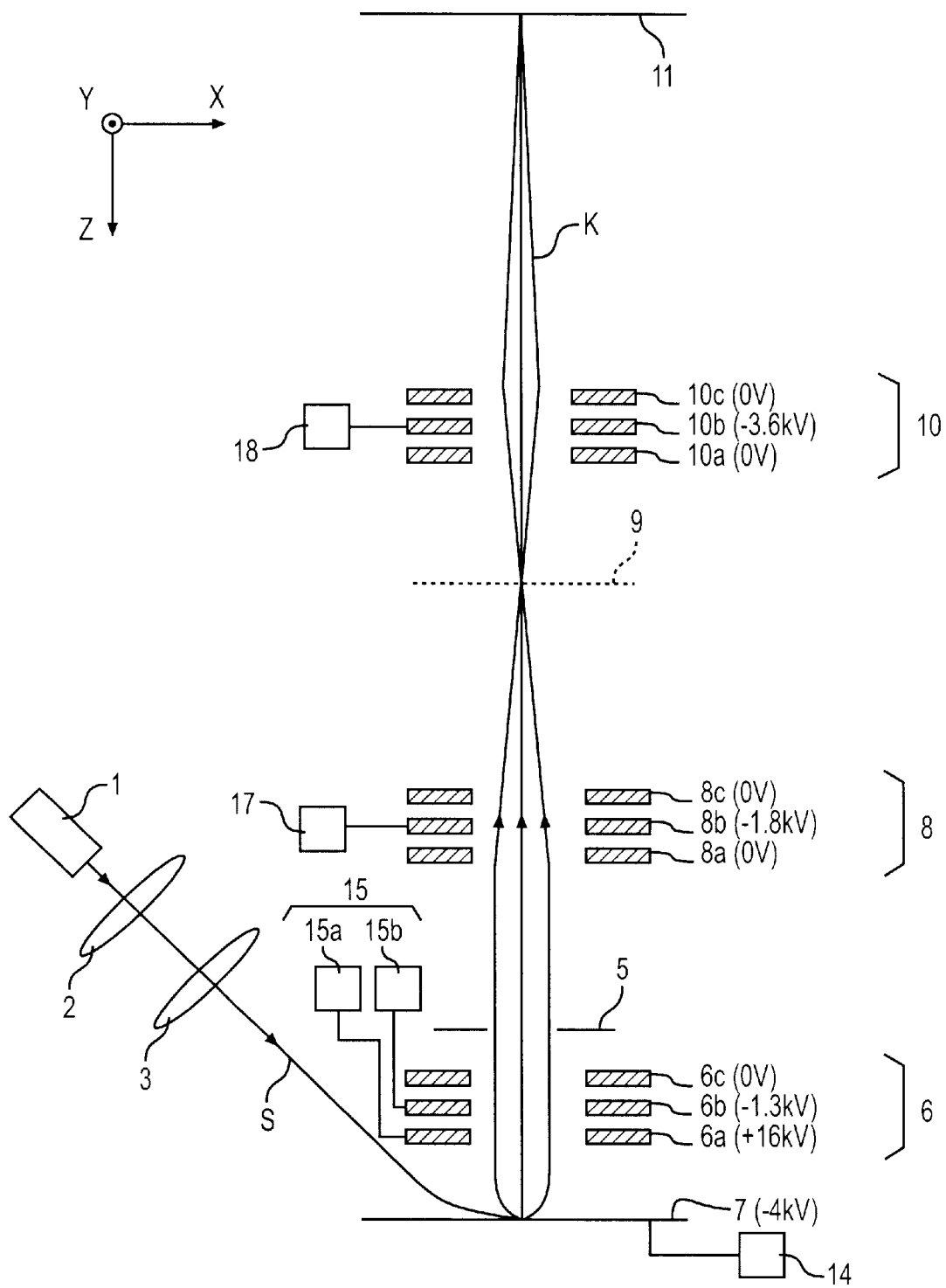
FIG. 2 is a diagram which illustrates an electron-optical system constructed according to a second embodiment of the present invention.
Figure 3:
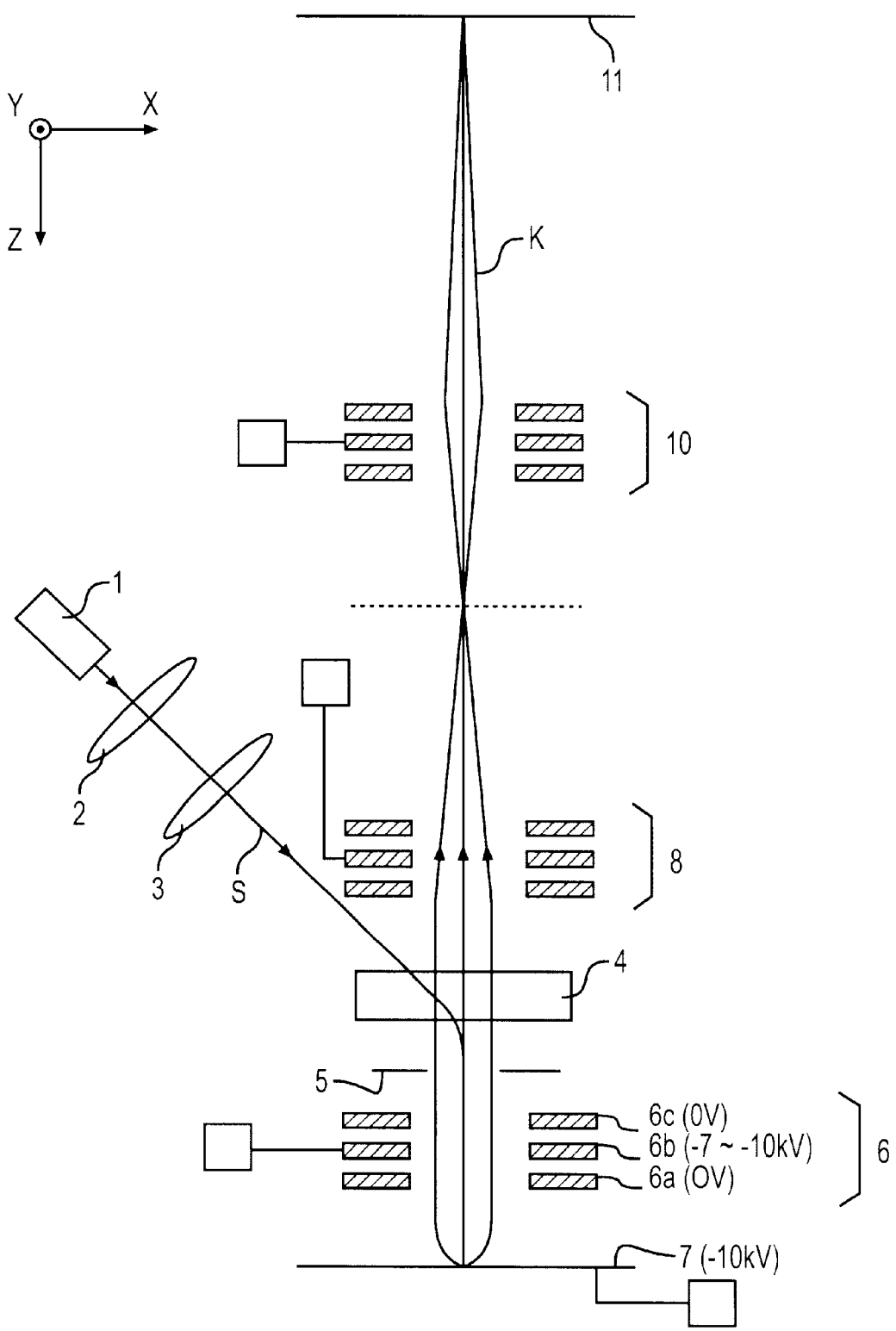
FIG. 3 is a diagram which illustrates a conventional electron-optical system.

Next, a second embodiment of the electron-optical system of the present invention is shown in FIG. 2. This second embodiment consists of a construction in which the beam separator 4 used in the above-mentioned first embodiment is eliminated. Furthermore, in this second embodiment, the irradiating electron beam S that is emitted from the electron gun 1 is caused to reach the sample 7 directly after passing through the illumination lenses 2 and 3. Afterward, the process up to the point at which the observational electron beam K emitted from the sample 7 reaches the electron beam detector 11 is the same as in the first embodiment, except that the beam does not pass through a beam separator 4. Here, the electron gun 1 and the illumination lenses 2 and 3 constitute the irradiation means. Furthermore, the cathode lens 6, aperture diaphragm 5, image-focusing lens front group 8 and image-focusing lens rear group 10 constitute the observation means.

In this second embodiment, as in the first embodiment, the potential applied to the sample 7 can be set at a relatively low value. Accordingly, the time required for the voltage rise can be shortened, so that the observational efficiency can be improved. Furthermore, in addition to the sample power supply 14, the potentials supplied from the power supplies of the illumination lenses 2 and 3, the image-focusing lens front-group power supply 17 and the image-focusing lens rear-group power supply 18 can also be set at relatively low values; accordingly, the cost of the apparatus as a whole can be lowered.

Thus, the first and second embodiments of the present invention make it possible to provide, at low cost, an electron-optical system with a high observational efficiency in which the observational magnification can be increased while maintaining the total electron path length and maintaining the observational electron yield and resolution.

(Third Embodiment)

Figure 4:
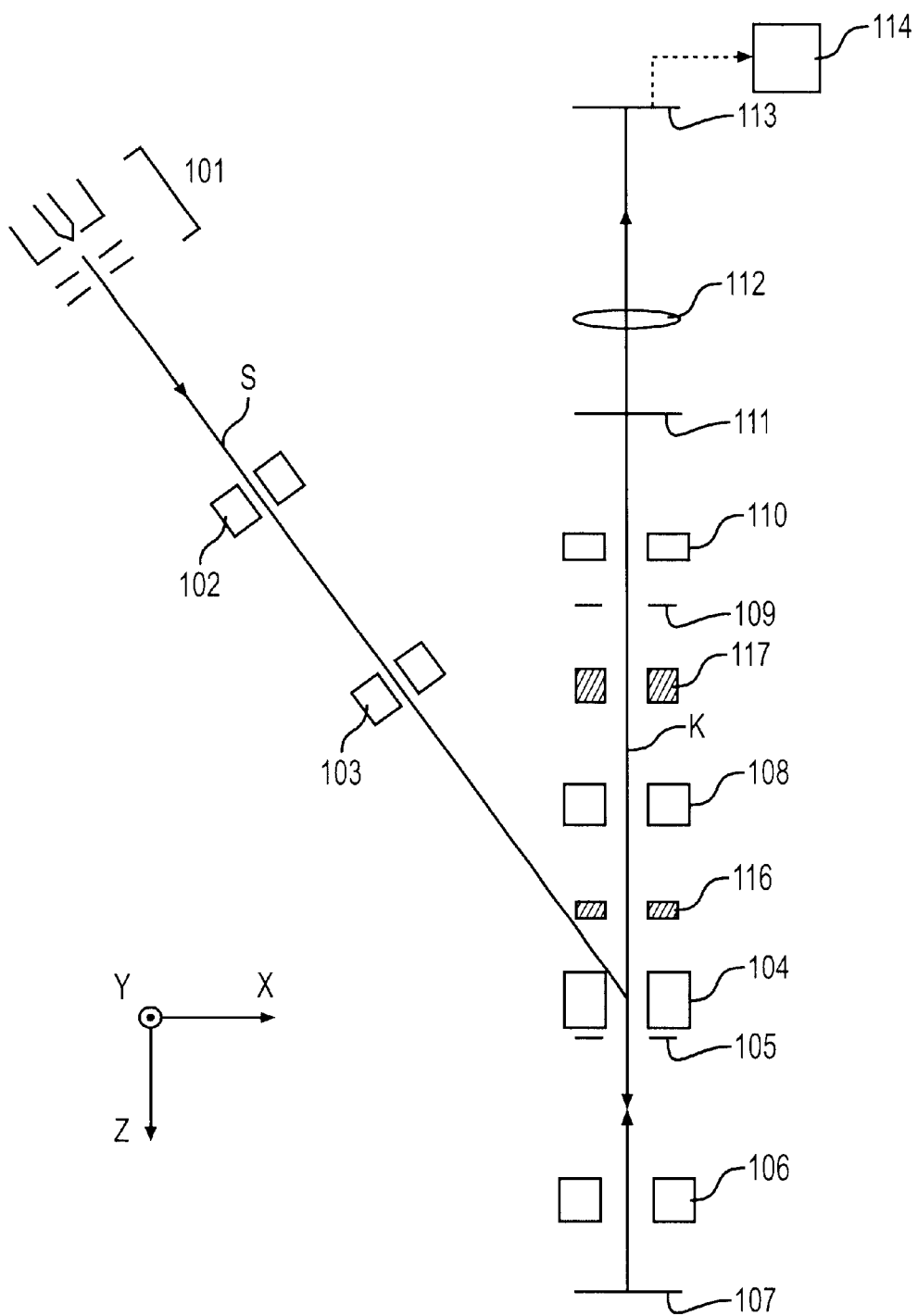
FIG. 4 is a diagram which illustrates an imaging electron microscope constituting a third embodiment of the present invention.

A third embodiment of the present invention will be described with reference to FIG. 4. The irradiating electron beam S emitted from the electron gun 101 is shaped by illumination lenses 102 and 103, and then enters an E-cross-B (beam separator) 104. The irradiating electron beam S deflected by the E-cross-B 104 passes through the aperture diaphragm 105, and is then directed onto the sample 107 via a cathode lens 106.

When the irradiating electron beam S is directed onto the sample 107, secondary electrons, reflected electrons and back-scattered electrons, etc., are emitted from the sample 107. Electrons of at least one of these types constitute an imaging electron beam K.

The imaging electron beam K emitted from the sample 107 passes through the cathode lens 106 and aperture diaphragm 105, and enters the E-cross-B 104. Then, the imaging electron beam K which passes through the E-cross-B 104 in a straight line as a result of the Wien condition being satisfied passes successively through a first stigmator 116, the image-focusing lens front group 108 and a second stigmator 117, after which this beam forms an intermediate image on a visual field diaphragm 109. The imaging electron beam K which passes through the visual field diaphragm 109 further passes through the image-focusing lens rear group 110, and forms an enlarged projected image on the electron beam detector 111.

Here, the first stigmator 116 and second stigmator 117 are (for example) electrostatic type octopoles. Furthermore, the first stigmator 116 is installed in the vicinity of the E-cross-B 104 so that the astigmatic difference is corrected with good efficiency. Meanwhile, the second stigmator 117 is installed between the image-focusing lens front group 108 and the visual field diaphragm 109, so that the magnification difference is corrected with good efficiency.

Furthermore, the illumination lenses 102 and 103, image-focusing lens front group 108 and image-focusing lens rear group 110 are electrostatic lenses such as einzel lenses, etc. The cathode lens 106 is also a lens in which the electrode installed on the side of the sample surface is biased to a positive potential with respect to the ground potential.

When the imaging electron beam K reaches the electron beam detector 111, the imaging electron beam K is converted into light. The light emitted from the electron beam detector 111, i. e., an optical image of the sample 107, passes through a relay lens 112, and is caused to be incident on an image pick-up element 113 such as a CCD, etc. The light incident on the image pick-up element 113 is converted into a photoelectric signal and transmitted to a control part 114.

Figure 5:
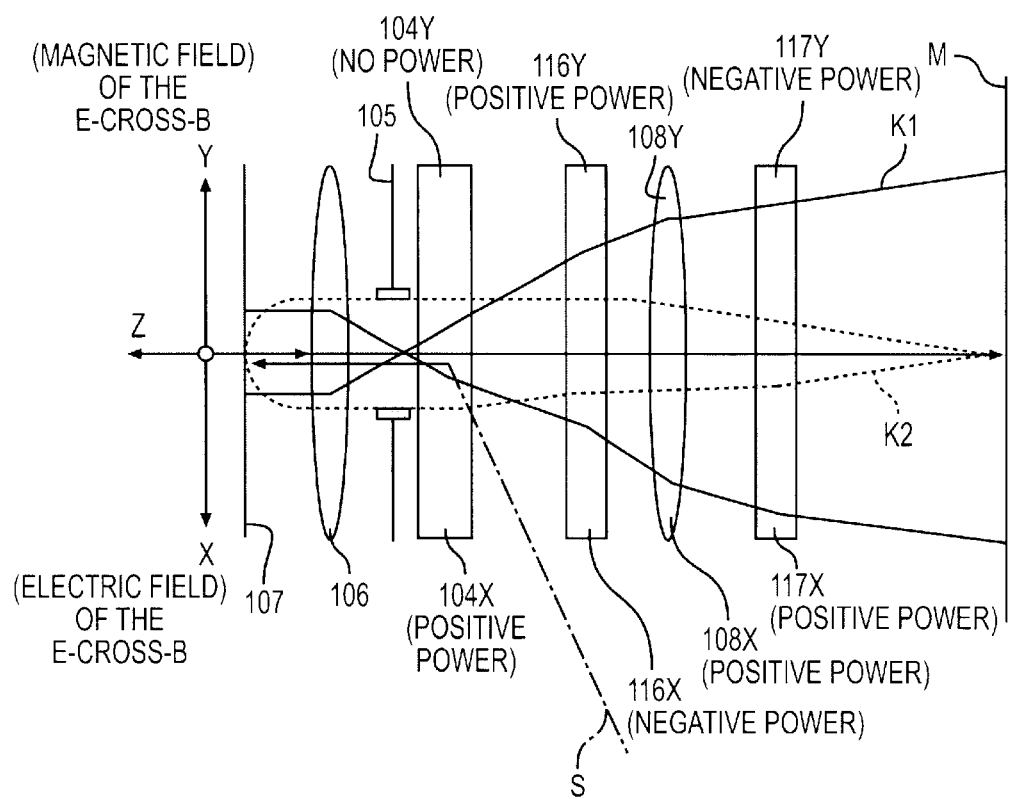
FIG. 5 is a diagram which illustrates the imaging means in the third embodiment of the present invention.

Next, FIG. 5 shows the imaging means of an imaging electron microscope constituting a third embodiment of the present invention, and this imaging means will be described. In FIG. 5, the track of the electron beam passing through the imaging means is shown divided into the X direction (direction of the electric field of the E-cross-B) and Y direction (direction of the magnetic field of the E-cross-B). Furthermore, the imaging electron beam emitted from the sample 107 is shown divided into a chief ray K1 indicated by a solid line, and maginal ray K2 indicated by a broken line. Here, the marginal ray K2 is in-axis marginal ray which is emitted from the aperture diaphragm 105 in an a focal system.

Below, the correction of the astigmatic difference and magnification difference by the first stigmator 116 and second stigmator 117 will be described in detail with reference to the same figure. The electron beam emitted from the sample 107 enters the E-cross-B 104 after passing through the cathode lens 106 and aperture diaphragm 105. As was described above, the electron beam inside the E-cross-B 104 receives positive power in the E-cross-B electric field direction 104X, and no power in the E-cross-B magnetic field direction 104Y. As a result, an astigmatic difference and magnification difference are generated in the magnetic field direction with respect to the electric field direction. The electron beam that has passed through the E-cross-B 104 subsequently forms an image on the intermediate image-focusing plane M after passing successively through the first stigmator 116, image-focusing lens front group 108 and second stigmator 117. This intermediate image-focusing plane M is located at the position of the visual field diaphragm 109.

Here, the first stigmator 116 is installed in the vicinity of the E-cross-B 104, and the second stigmator 117 is installed between the image-focusing lens front group 108 and the intermediate image-focusing plane M. As a result, there is a great difference between the spacing of the incidence height of the chief ray K1 and the incidence height of the marginal ray K2 at the position of the first stigmator 116 and the spacing of the chief ray K1 and marginal ray K2 at the position of the second stigmator 117. Thus, of the two differences generated by the E-cross-B 104, the astigmatic difference is corrected with good efficiency mainly by the first stigmator 116, while the magnification difference is corrected with good efficiency mainly by the second stigmator 117.

In concrete terms, in order to correct the astigmatic difference of the marginal ray K2 in the first stigmator 116, a voltage is applied so that negative power is generated in the first stigmator electric field direction 116X, and so that positive power is generated in the first stigmator magnetic field direction 116Y. In such a case, since the chief ray K1 is over-corrected, a magnification difference which is spread in the electric field direction is generated. According to numerical analysis under prescribed conditions, this magnification difference is such that when the magnification in the magnetic field direction is 1, the magnification in the electric field direction is 1.2.

Thus, in order to further correct the over-corrected chief ray K1 generated by the first stigmator 116, a voltage is applied in the second stigmator 117 so that positive power is generated in the second stigmator electric field direction 117X, and so that negative power is generated in the second stigmator magnetic field direction 117Y.

Thus, in the present embodiment, by balancing the correction of the first stigmator 116 and the correction of the second stigmator 117, it is possible to correct the astigmatic difference and magnification difference simultaneously and with good efficiency.

Furthermore, in the present embodiment, the correction of the differences generated by the E-cross-B 104 was described; however, differences arising from other causes, i. e., differences attributable to mechanical tolerances or contamination over time, etc., can also be easily corrected by adjusting the voltages applied to the first stigmator 116 and second stigmator 117.

Furthermore, in the imaging means of the present embodiment, a synthesized positive power is generated by the E-cross-B 104, first stigmator 116 and second stigmator 117; in this case, the desired magnification and total length can be insured by adjusting the focal length of the image-focusing lens front group 108, i. e., the positive power. Furthermore, if an imaging means in which the magnification and total length are thus maintained at optimal values is used, a telecentric optical system with little aberration can be constructed.

Furthermore, in the imaging microscope of the present embodiment, an image with an equal longitudinal-lateral ratio was formed without generating an astigmatic difference. However, it would also be possible to form images with different preset longitudinal-lateral ratios.

Thus, in the present embodiment, any astigmatic difference or magnification difference can be corrected, so that a high-resolution imaging microscope which is superior in terms of durability can be provided at low cost.

Specifically, even if an easily manufactured low cost type E-cross-B is used, an imaging electron microscope which allows easy and reliable simultaneous correction of the astigmatic difference and magnification difference that are generated can be obtained. Furthermore, any astigmatic difference or magnification difference arises from mechanical causes such as manufacturing error, etc., can also be simultaneously corrected; accordingly, an imaging electron microscope which is easy to manufacture, and in which the mechanical tolerances of the apparatus as a whole are relaxed, can be obtained. Furthermore, any astigmatic difference or magnification difference generated by contamination with irradiating particles, etc., can also be simultaneously corrected; accordingly, an imaging electron microscope which shows a high durability with respect to changes over time can be obtained.

(Fourth Embodiment)

Below, a fourth embodiment of the present invention will be described with reference to the attached figures.

Figure 6:
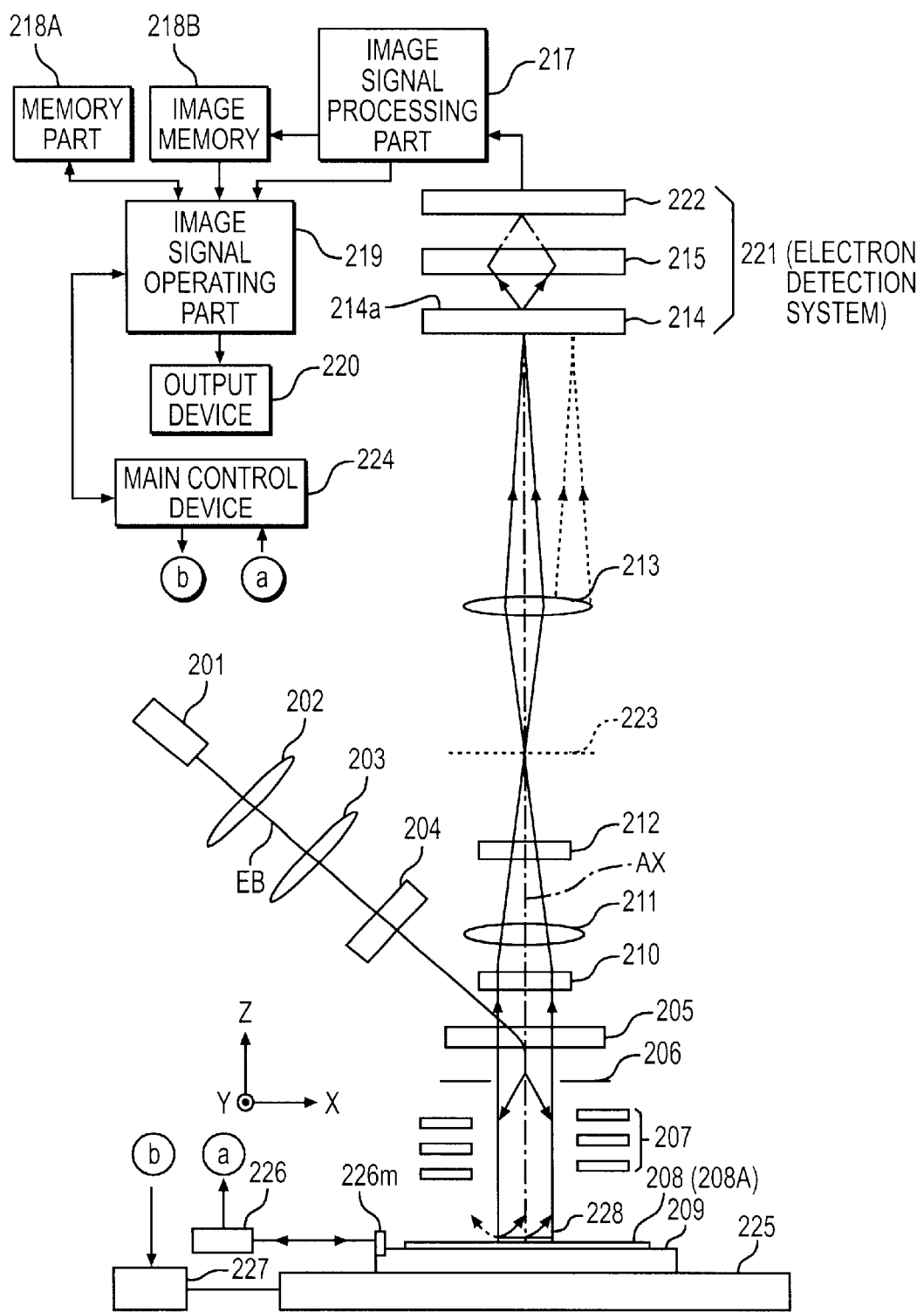
FIG. 6 is a schematic structural diagram which illustrates an imaging electron microscope used in a fourth embodiment of the present invention.

FIG. 6 shows the schematic structure of the imaging electron microscope of the present embodiment. In this FIG. 6, an electron beam EB emitted from the electron gun 201 is shaped via a first illumination lens 202, second illumination lens 203 and electrostatic type first aberration correcting system 204; afterward, this beam is deflected by a beam separator 205 in the direction perpendicular to the surface of the sample 208 which is carried on an XY stage 209. The illumination lenses 202 and 203 are electrostatic lenses. Furthermore, the electron beam EB deflected by the beam separator 205 forms a cross-over image at the center of the aperture of the aperture diaphragm 206; this beam is then decelerated by a decelerating electric field formed between the cathode lens 207 and the sample 208, and illuminates the visual field (detected region) 228 on the surface of the sample 208 by means of a Koehler illumination system. The illumination system consists of the electron gun 201 to the cathode lens 207. Here, in the cathode lens 207, the electrode installed closest to the surface of the sample 208 is biased to a positive potential with respect to the ground potential. Furthermore, the sample 208 in this example is a wafer consisting of silicon or SOI (silicon on insulator), etc. Semiconductor device circuit patterns are formed on this wafer.

In the following description, the Z axis is taken in the direction perpendicular to the surface of the sample 208, the X axis is taken parallel to the plane of the page in FIG. 6 within a plane parallel to the surface of the sample 208, and the Y axis is taken in the direction perpendicular to the plane of the page in FIG. 6. In this case, the visual field 228 on the sample 208 is a long, slender two-dimensional region in which the width in the X direction is greater than the width in the Y direction (see FIG. 7).

Furthermore, secondary electrons or reflected electrons (hereafter referred to as "detected electrons") generated by the sample 208 as a result of irradiation by the electron beam EB are drawn upward by the decelerating electric field formed between the cathode lens 207 and sample. After passing through the cathode lens 207, the aperture of the aperture diaphragm 206 and the beam separator 205, these electrons pass through an electrostatic type second aberration correcting system 210, a first image-focusing lens 211 consisting of an electrostatic lens, and an electrostatic type third aberration correcting system 212, and form a tentative image of the visual field 228 on the intermediate image-focusing plane 223. Then, the detected electrons that pass through the intermediate image-focusing plane 223 further pass through a second image-focusing lens 213 consisting of an electrostatic lens, and form an enlarged image of the visual field 228 on the entry side of a MCP (micro-channel plate) 214. This enlarged image formed by the detected electrons is converted into a fluorescent light image (optical image) by a fluorescent surface 214*a* on the emission side of the MCP 214. The light beam leaving the fluorescent surface 214*a* passes through an optical lens 215, and forms an enlarged image based on the light of the pattern within the visual field 228 on the image pick-up surface of a CCD type image pick-up element 222 using a TDI (time delay integration) system (hereafter referred to as a "TDI sensor").

Furthermore, for example, a Wien filter which generates a prescribed electric field and magnetic field as disclosed in K. Tsuno: Ultramicroscopy 55, pp. 127–140 (1994) can be used as the beam separator 205 which is used as a separating system to separate the electron beam incident on the sample 208 and the detected electrons from the sample 208.

An image-focusing system consists of the cathode lens 207 to the second image-focusing lens 213, which are lined up along the optical axis AX parallel to the Z axis. An electron detection system 221 which converts the electron image into a light-based image, and which further performs a photo-electric conversion, is formed by the MCP 214, optical lens 215 and TDI sensor 222. Furthermore, the image signals output from the respective pixels of the TDI sensor 222 are ordinarily stored in a VRAM type image memory 218B from an image signal processing part 217. Then, after data for a prescribed range has been accumulated, this data is successively read into an image signal operating part 219 consisting of a microprocessor and RAM, etc. A lens system which projects the image of the fluorescent surface 214*a* as a whole onto the TDI sensor 222 may be used as the optical lens 215; however, it would also be possible to conduct the light of the fluorescent surface 214*a* "as is" onto the TDI sensor 222 using an optical fiber bundle instead.

Furthermore, in cases where operations are performed in real time, the image signal processing part 217 sends image signals from the TDI sensor 222 directly to the image signal operating part 219. The image signal operating part 219 corrects the level of the image signals by performing operations (described later) on the image signals using a standard image signal read out from the memory part 218A; afterward, processing which converts the signals into binary data is performed at a prescribed threshold value, and this data is output to an output device 220 such as a CRT display, etc. The output device 220 is also equipped with an image memory, and defective portions, etc., of the surface of the sample 208, for example, are displayed on the display part of the output device 220. Furthermore, a combination of a magnetic memory device and RAM, etc., is used as the memory part 218A.

The XY stage 209 on which the sample 208 that is the object of observation is carried and fastened in place by (e. g.) an electrostatic chucking system is placed on the upper surface of a base 225, and can be continuously moved in the X and Y directions by (for example) a linear motor. Furthermore, step movements can also be performed by means of this continuous movement. Furthermore, in order to perform coordinate measurements on the XY stage 209 (sample 208), an X-axis moving mirror 226*m* and Y-axis moving mirror (not shown in the figures) are fastened to the upper end of the XY stage 209, and laser beams from a laser interferometer 226 are directed toward the moving mirrors 226*m*, etc., parallel to the X axis and Y axis. In the laser interferometer 226, interference light between the returning laser beam and the corresponding reference laser beam (not shown in the figures) is photo-electrically detected, so that the X and Y coordinates of the X stage 209 (sample 208) are detected. This positional information is sent to a main control system 224 consisting of a computer; in this main control system 224, the moving speed and positioning of the XY stage 209 are controlled via a stage driving device 227 based on the positional information.

Furthermore, during observation of the sample, as is shown in FIG. 7(*a*), the region that is the object of inspection, in which circuit patterns are formed on the sample 208, is divided into a plurality of observation regions 242A through 242G in the X direction at a pitch that is slightly smaller than the width of the visual field 228 in the X direction. Furthermore, the observation region 242A of the sample 208 is first scanned along the track 241 in the −Y direction with respect to the visual field 228 by moving the XY stage 209, which is used as a scanning mechanism in FIG. 6, so that an image of the observation region 242A is picked up. Next, the XY stage 209 is caused to perform a step movement so that the observation region 242B is moved to a point in front of the visual field 228; then, the observation region 242B is scanned in the +Y direction with respect to the visual field 228, so that an image of the observation region 212B is picked up. Thus, the above-mentioned step movements and continuous movements (scanning) are repeated, so that the observation regions 242A through 242G are relatively scanned by the visual field 228, thus causing an image of the entire region constituting the object of inspection on the surface of the sample 208 to be observed.

When the surface of the sample 208 is thus relatively scanned by the visual field 228 in the Y direction (scanning direction), the TDI sensor 222 in FIG. 6 integrates the image of the visual field 228 in the scanning direction in synchronization with the relative scanning. As a result, an image signal with a good SN ratio is obtained; the principle behind this will be explained below.

Figure 7A:
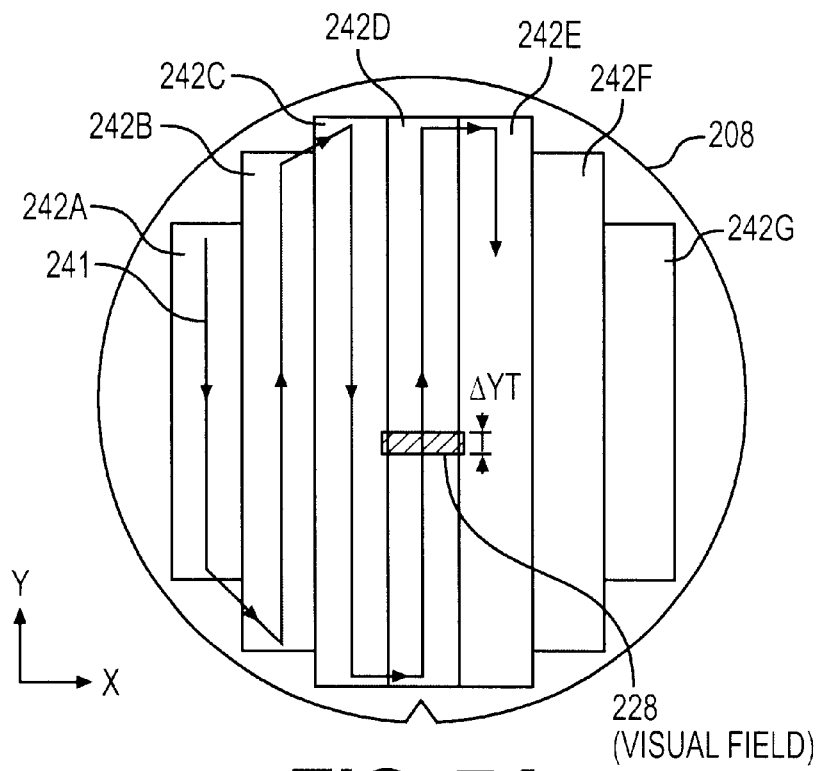
FIG. 7(a) is a plan view which is used to illustrate the scanning and observation of the sample 208 with respect to the visual field 228 in FIG. 6.
Figure 8:
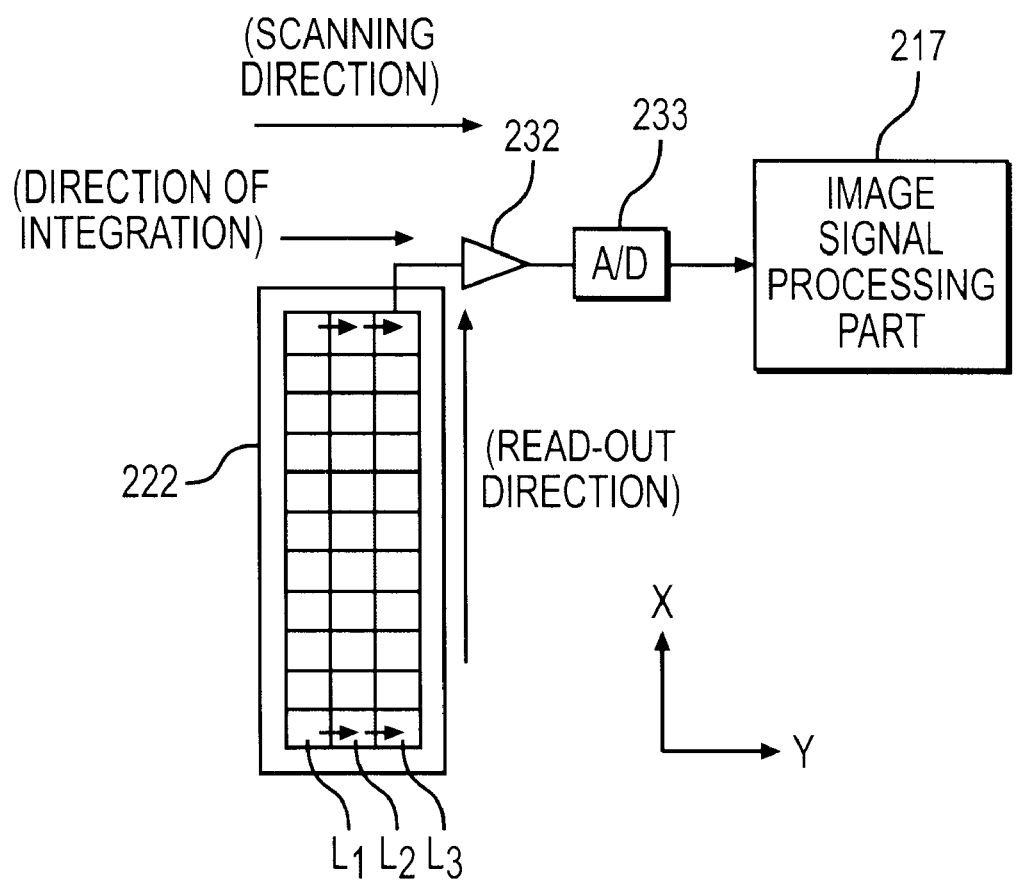
FIG. 8 is a diagram which illustrates the TDI sensor 222 shown in FIG. 6.

FIG. 8 shows the TDI sensor 222 used in the imaging electron microscope of the present embodiment. In FIG. 8, the directions corresponding to the X direction and Y direction in FIG. 7(a) are respectively taken as the X direction and Y direction (scanning direction). The TDI sensor 222 has two-dimensional pixel regions which are long and slender in the X direction in correspondence with the image of the visual field 228. The long, slender pixel regions are constructed from a plurality of lines L1 through L3 that are lined up in the Y direction at a prescribed pitch; lines L1 through L3 are each constructed from a plurality of pixels lined up in the X direction at a prescribed pitch. The TDI sensor 222 can read out the image signals (charges) of the pixels in the line L3 positioned in the vicinity of the optical axis AX at an arbitrary timing in the X direction, and can then immediately afterward successively move the image signals (charges) of the lines L2 and L1 to the lines L3 and L2 in the Y direction. In the lines L3 and L2, accumulation of the charges is subsequently initiated; as a result, the image signals are successively integrated in the Y direction.

Specifically, in the TDI sensor 222, during the time period extending from the time that the same region on the sample 208 enters the region corresponding to the first line L1 within the visual field 228 to the time that this region leaves the region corresponding to the third line L3 when the sample 208 is scanned with respect to the visual field 228, and therefore with respect to the TDI sensor 222, the above-mentioned same region is successively imaged by the respective lines L1 through L3, for a number of lines corresponding to the number of lines L1 through L3 possessed by the TDI sensor 222 (three lines in FIG. 8), and the image signals obtained are integrated. Then, the image signal finally obtained by integration and imaging by line L3 inside the TDI sensor 222 (i. e., the integrated image signal) is sent to the image signal processing part 217 via a variable-gain amplifier 232 and A/D (analog/digital) converter 233. Then, the image signals successively output from line L3 are stored in an image memory 218B (for example), so that an image signal corresponding to the image of a two-dimensional region on the surface of the sample 208 is constructed.

Figure 9A:
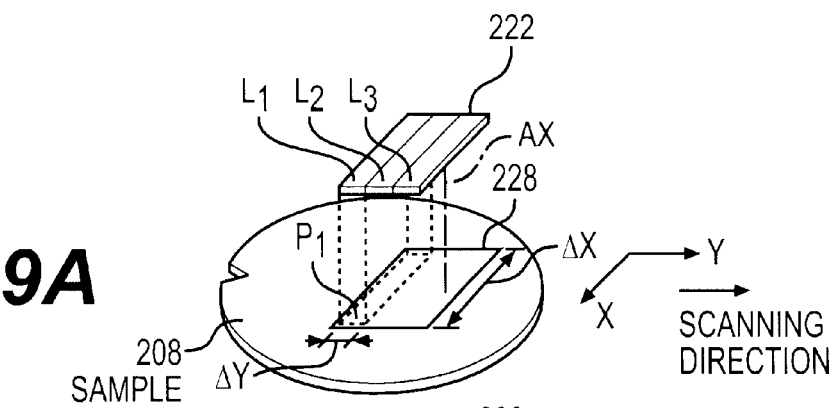
FIG. 9 is a diagram which is used to illustrate the operation that takes place when the image within the visual field 228 is picked up using the TDI sensor 222.
Figure 9B:
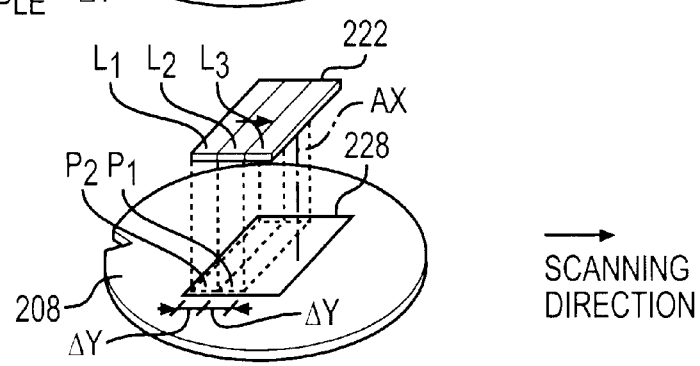

FIG. 9 shows the positional relationships that obtain when the sample 208 is imaged while being scanned with respect to the visual field 228, and thus with respect to the TDI sensor 222. In FIG. 9(a), the first line L1 of the TDI sensor 222 detects an image of a region P1 with a width of $\Delta X$ in the X direction and a width of $\Delta Y$ in the Y direction on the surface of the sample 208 within the visual field 228, and generates an image signal. This image signal is transmitted to the second line L2. Next, as is shown in FIG. 9(b), when the sample 208 is moved by a distance of $\Delta Y$ in the Y direction so that the region P1 moves to a region conjugate with the second line L2, an image of the region P1 is detected by the second line L2, and an image signal is generated. This image signal is generated in a form in which the signal is added to the image signal transmitted from the first line L1, and this image signal of the second line L2 is transmitted to the third line L3. At this time, the first line L1 detects an image of a region P2 with a width of $\Delta Y$ which is adjacent to the region P1 on the sample 208, and generates an image signal, which is transmitted to the second line L2.

Figure 9C:
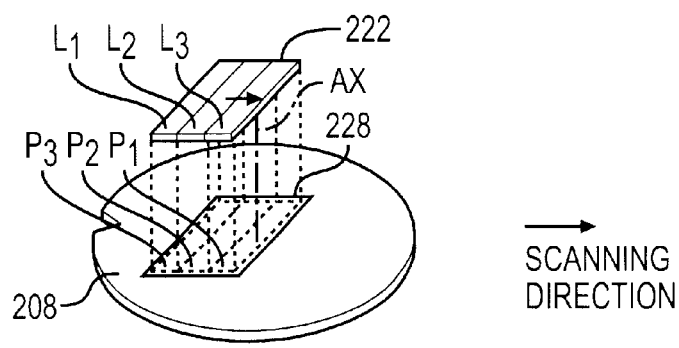

Then, as is shown in FIG. 9(c), when the region P1 moves to a region conjugate with the third line L3, the third line L3 detects an image of the region P1 and generates an image signal in a form in which this signal is added to the image signal of the region P1 previously transmitted from the second line L2. In this case, in the second line L2 and first line L1, images of the region P2 and a region P3 with a width of $\Delta Y$ which is adjacent to this region P2 are respectively picked up. As a result, image signals of regions with a width of $\Delta Y$ on the surface of the sample 208 are successively generated.

Thus, as a result of the use of the above-mentioned TDI sensor 222, image signals representing images of the same region on the sample 208, which are generated by the respective lines L1 through L3, are integrated and output; accordingly, even in cases where the quantity of detected electrons from the sample 208 is small (i. e., cases in which the SN ratio is small), an image signal with a relatively large signal level can be obtained. Furthermore, the following advantage is also obtained: namely, the effect of variations in the detection sensitivity for the respective pixels of the MCP 214 in the electron detection system 221 and the respective pixels of the TDI sensor 222 is averaged out in the direction of integration (i. e., the Y direction). Furthermore, in the present example, for the sake of simplicity of description, the TDI sensor 222 in FIG. 8 was described as a sensor having 3×10 pixels; in actuality, however, the TDI sensor 222 has (for example) approximately 100×1000 pixels (100 lines×1000 pixels).

Figure 14:
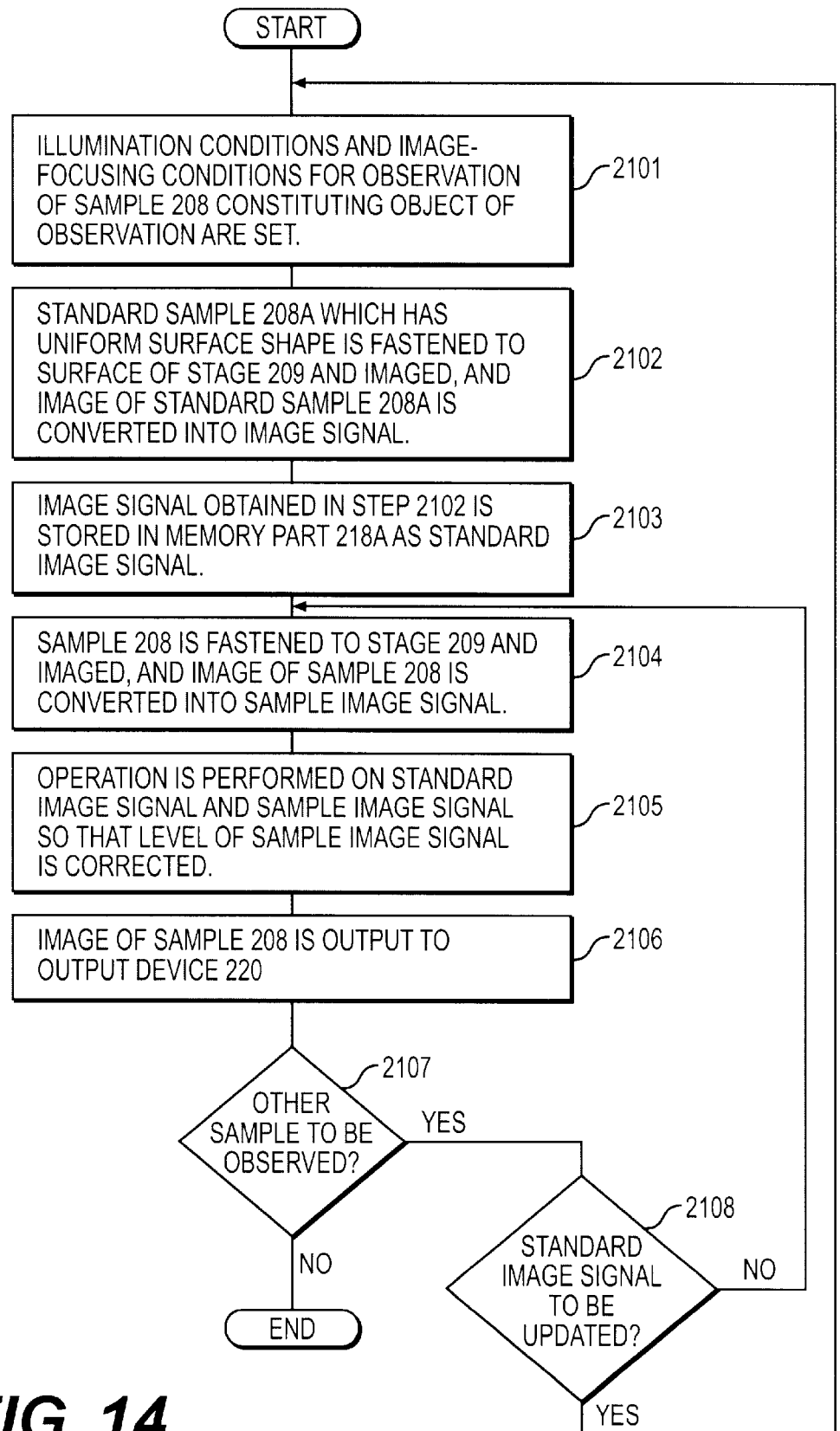
FIG. 14 is a flow chart which illustrates one example of the operation that is performed when a sample is observed using the imaging electron microscope of the fourth embodiment of the present invention.

Next, the method used to observe samples by means of the imaging electron microscope of the present example will be described with reference to the flow chart shown in FIG. 14.

Figure 10:
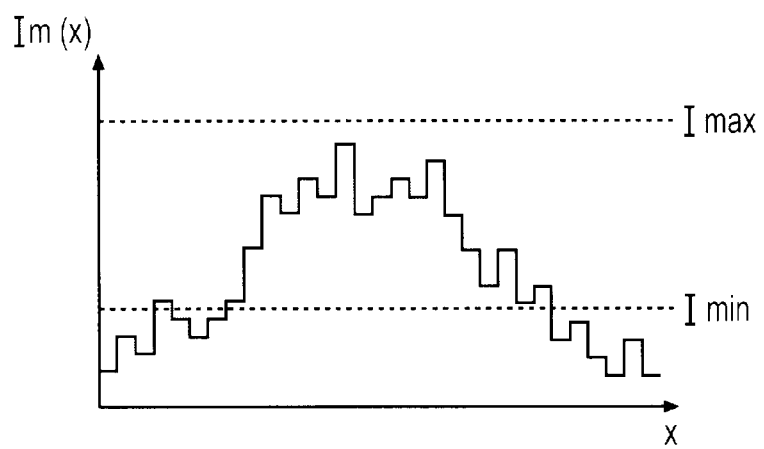
FIG. 10 is a diagram which illustrates one example of the image signal of the sample within the visual field 228 shown in FIG. 6.

First, in step 2101, the sample 208 constituting the object of observation is placed on the XY stage 209 shown in FIG. 6, and is fastened in place by electrostatic chucking, etc. Afterward, the irradiation system (electron gun 201 through cathode lens 207) and image-focusing system (cathode lens 207 through second image-focusing lens 213) are adjusted, so that the illumination conditions and image-focusing conditions such as the intensity (brightness) of the electron beam used to observe the sample 208, the size of the visual field and the observational magnification, etc., are set. For example, these conditions are set by the operator via the main control device 224. In this case (for example), as is shown in FIG. 10, the brightness of the electron gun 201 and the size of the visual field 228 are adjusted so that the signal level of the image signals Im(x) output from the electron detection system 221 is at least at a minimum level Imin which makes it possible to obtain a sufficiently large SN ratio throughout the entire region of the width of the visual field 228 in the X direction, and does not exceed the saturation level Imax of the respective pixels of the TDI sensor 222. In FIG. 10, the horizontal axis indicates a position x obtained by converting the X coordinate on the TDI sensor 222 into the value of the X coordinate on the visual field 228, and the vertical axis indicates the image signals Im(x) at this position x.

Figure 7B:
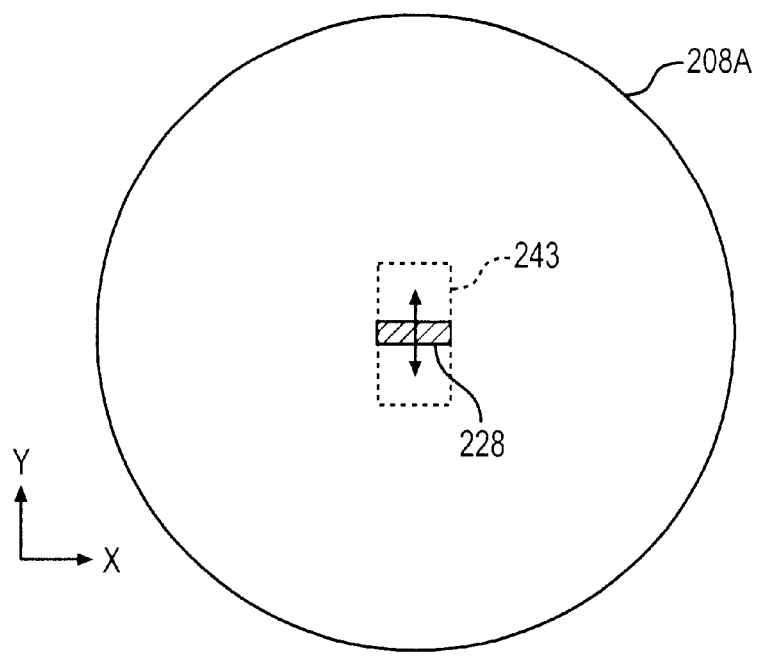
FIG. 7(b) is a plan view which illustrates a standard sample 208A.

Next, proceeding to step 2102, after a standard sample 208A which has a uniform surface shape is placed on and fastened to the XY stage 209, an image of a prescribed region on the surface of this sample is picked up. In the present example, a silicon wafer with good surface flatness (i. e., a super-flat wafer) which has approximately the same shape as the sample 208 is used as the standard sample 208A. Furthermore, it would also be possible to use a super-flat wafer on which a prescribed metal film is vacuum-evaporated, etc., as the standard sample 208A. When the standard sample 208A is imaged, image signals from the TDI sensor 222 are input into the image signal operating part 219 via the image signal processing part 217 while a rectangular observation region 243 on the surface of the standard sample 208A is scanned relative to the visual field 228 as shown in FIG. 7(b) by moving the XY stage 209 shown in FIG. 6 in the +Y direction (or −Y direction). In this case, image signals for a plurality of lines obtained for each of a plurality of regions obtained by dividing the observation region 243 by the width ΔY in the Y direction (see FIG. 9) are averaged by the image signal operating part 219, so that slight irregularities in brightness shown by the image of the standard sample 208A are averaged in the scanning direction, thus making it possible to obtain a highly uniform image signal of the standard sample 208A. Then, proceeding to step 2103, the image signal obtained by the averaging performed by the image signal operating part 219 is stored as a standard image signal in (for example) a RAM inside the memory part 218A.

Furthermore, the TDI sensor 222 in the present example has a plurality of lines of pixels; accordingly, an image within the visual field 228 can be picked up at one time by the TDI sensor 222 in a state in which the standard sample 208A is caused to be stationary, without scanning the broad observation region 243 shown in FIG. 7(b) relative to the visual field 228. In this case, after imaging, an operation in which the image signals of the plurality of lines are moved in the Y direction one row at a time and are then read out in the X direction as shown in FIG. 8 is repeated, and the image signals that are successively read out are averaged, thus producing a standard image signal which is averaged in the Y direction within the visual field 228.

Here, the position along the X coordinate within the visual field 228 is designated as x, the intensity distribution of the electron beam produced by the above-mentioned irradiation system at position x is designated as G(x), and the detection sensitivity distribution for each pixel of the electron detection system 221 at the position conjugate with position x is designated as D(x). Then, if the standard image signals obtained when the standard sample 208A is observed in an ideal state in which the intensity distribution G(X) and detection sensitivity distribution D(x) are respectively constant (i. e., assumed to equal 1) are designated as IO(x), the standard image signals IOm(x) actually obtained from the standard sample 208A can be expressed by the following equation:

$$IOm(x) = G(x) \cdot D(x) \cdot IO(x) \qquad (1)$$

Furthermore, patterns similar to the circuit patterns formed on the sample 208 constituting the object of observation may be formed in some region of the standard sample 208A. In such a case, the setting of the measurement conditions performed in step 2101 can be accomplished utilizing the region in which the above-mentioned patterns are formed on the standard sample 208A; afterward, the generation of a standard image signal performed in steps 2102 and 2103 can be accomplished merely by moving the XY stage 209 so that a region in which no patterns are formed on the standard sample 208A is caused to move into the visual field 228. Furthermore, in cases where image differences (defective areas, etc.) between the sample 208 and the standard sample 208A are to be measured, the standard sample 208A does not necessarily have to be a sample with a uniform surface shape.

Next, proceeding to step 2104, after the sample 208 constituting the object of observation is placed on and fastened to the surface of the XY stage 209, images of the region constituting the object of detection on the surface of the sample 208 are successively picked up by scanning the sample 208 relative to the visual field 228 as shown in FIG. 7(a), and images of a plurality of regions (see FIG. 9) obtained by dividing the region constituting the object of detection by the width ΔX in the X direction and the width ΔY in the Y direction are converted into respective image signals. Since the image signals thus produced by this conversion for each of the regions can be viewed as functions of the respective positions x in the X direction within the visual field 228, these image signals are typically called sample image signals Im(x). The sample image signals Im(x) are successively stored in the image memory 218B.

Here, if the sample image signals obtained in a case where the sample 208 is observed in an ideal state in which the intensity distribution G(x) of the electron beam within the visual field 228 and the detection sensitivity distribution D(x) of the electron detection system 221 are respectively constant (=1) are designated as I(x), then the actual sample image signals Im(x) can be expressed by the following equation:

$$Im(x) = G(x) \cdot D(x) \cdot I(x) \qquad (2)$$

Then, proceeding to step 2105, the image signal operating part 219 shown in FIG. 6 determines the quotient signals S(x) as follows by dividing the sample image signals Im(x) successively read out from the image memory 218B respectively by the standard image signals IOm(x) read out from the memory part 218A. In this case, Equation (1) and Equation (2) are used.

$$S(x) = Im(x)/IOm(x) \qquad (3)$$
$$= I(x)/IO(x)$$

Here, the standard image signals IO(x) may be viewed as a constant value C, so that the quotient signals S(x) can be expressed in a form proportional to the sample image signals I(x) obtained in an ideal state, as shown by the following equation:

$$S(x) = Im(x)/C \qquad (4)$$

As a result of the quotient signals S(x) thus being determined by dividing the actual sample image signals Im(x) by the standard image signals IOm(x), the effects of the intensity distribution G(x) of the electron beam within the visual field 228 and the detection sensitivity distribution D(x) of the electron detection system 221 can be eliminated. Furthermore, instead of performing the division of Equation (3), it would also be possible to determine the reciprocals 1/IOm(x) of the standard image signals IOm(x) in the image signal operating part 219, store these reciprocals in the memory part 218A, and determine the products of these reciprocals with the sample image signals Im(x). Furthermore, adjustment of the signal level may be performed as desired by multiplying a normalization coefficient C0 with the quotient signals S(x) as shown by the following equation:

$$C0 \cdot S(x) = I(x) \cdot C0/C \qquad (5)$$

Figure 11:
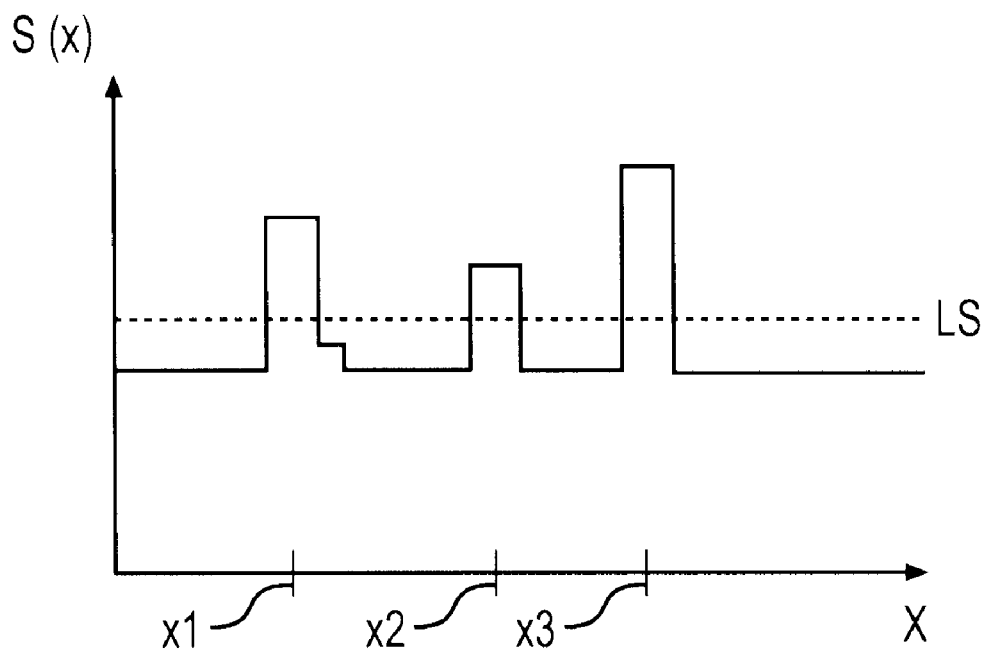
FIG. 11 is a diagram which is used to illustrate the binary processing of the image signal.

Then, proceeding to step 2106, the image signal operating part 219 generates image signals S(x)' which have a high level of "1" in areas equal to or greater than a prescribed threshold level SL and a low level of "0" in areas smaller than this threshold level SL, as shown in FIG. 11, from the quotient signals S(x) or C0·S(x) whose signal levels have been corrected, and sends these image signals S(x)' to the output device 220. In the output device, the image signals S(x)' are displayed on the display part with the areas having a high level of "1" appearing as bright areas, and the areas having a low level of "0" appearing as dark areas.

In the output device 220, respective binarized images are displayed on a screen corresponding to the region constituting the object of inspection on the sample 208 shown in FIG. 7(a), so that (for example) areas in which there are defects in the circuit patterns are displayed as bright areas; accordingly, the areas in which defects are present can be quickly and easily ascertained. For example, in the quotient signals S(x) shown in FIG. 11, it is seen that defects are present at positions x1, x2 and x3. Furthermore, in cases where a different sample is not observed in step 2107, observation is completed, while in cases where a different sample is observed, a judgement is made in step 2108 as to whether or not the standard image signals are to be updated. In cases where the standard image signals are not to be updated, the processing returns to step 2104, and a sample constituting a different object of observation is placed on the XY stage 209 and observed. Furthermore, in cases where updating of the standard image signals is to be performed, the processing returns to step 2101 from step 2108, and the illumination conditions and focusing conditions for observation are reset. Furthermore, the intensity distribution G(x) of the electron beam within the visual field 228 and the detection sensitivity distribution D(x) of the electron detection system 221 may vary gradually over time as the imaging electron microscope is used; accordingly, it is desirable that the standard image signals be periodically updated.

Thus, in the present example, the effects of variation in the intensity distribution of the electron beam created by the irradiation system and variation in the detection sensitivity distribution caused by variation in the electron-light conversion efficiency and photoelectric conversion efficiency, etc., of the electron detection system 221 are eliminated, so that images that are close to the true state of the sample 208 can be accurately observed. Furthermore, in the present example, the intensity distribution of the electron beam in the X direction with respect to the visual field 228 is a more or less gaussian distribution. In this case, the intensity distribution of the electron beam is large in the central portion of the fluorescent surface 214a of the MCP 214 shown in FIG. 6; as a result, a drop in the detection sensitivity (drop in gain) tends to occur in this central portion. However, even if the detection sensitivity drops in the central portion of the fluorescent surface 214a in this manner, the effect of this drop in the detection sensitivity is taken into account by using standard image signals in the present example; accordingly, there is the advantage of allowing the observation of accurate images of the sample 208 at all times.

Furthermore, the correction of the signal level of the sample image signals by the above-mentioned operation, the binarization processing using a prescribed threshold value, and the image output performed by the output device 220, are performed for blocks of data after a prescribed quantity of data has been accumulated. However, it would be possible instead to perform these operations in real time each time that an image signal for a slit-form region (region corresponding to one line) of width ΔX×width ΔY in FIG. 9(a) is obtained.

In the present example, furthermore, a TDI sensor 222 was used as the image pick-up element of the electron detection system 221; however, the present invention can also be applied in cases where an image pick-up element of the CCD type, etc., with pixels arranged in two dimensions, or a line sensor of the CCD type, etc., is used as the image pick-up element.

A case will be briefly described in which (for example) a two-dimensional image pick-up element which has rows of pixels arranged in n lines (n=2, 3, 4, . . . ) in the direction corresponding to the Y direction in a region corresponding to the visual field 228 on the sample 208 in FIG. 7(a), and which can read out the image signals of the respective lines independently in a direction corresponding to the X direction, is used as the image pick-up element. In this case, if the width in the Y direction of the visual field 228 is designated as ΔYT, then images of the visual field 228 in a state in which the standard sample 208A in FIG. 7(b) is caused to be stationary are first picked up, and n image signals respectively read out from the n lines of pixels of the image pick-up element are stored as n standard image signals. Next, when the sample 208 is observed, an image of the pattern within the visual field 228 is picked up by the two-dimensional image pick-up element each time that the sample 208 is caused to perform a step movement of ΔYT in the Y direction in FIG. 7(a).

Then, the sample image signals obtained from the n lines of pixels of the image pick-up element for each region with a width of ΔYT in the Y direction are respectively divided by the corresponding n standard image signals, so that a correction is made for the effects of the electron beam intensity distribution and detection sensitivity distribution. If a two-dimensional image pick-up element is thus used, the observation of the sample 208 can be performed efficiently in a short period of time.

Thus, in the imaging type observation method of the present embodiment, the following advantage is obtained: namely, the effects of variation in the intensity distribution of the charged-particle beam within the visual field and variation in the detection sensitivity distribution of the charged-particle beam detection system can be reduced, so that the sample can be observed in a state closer to the actual image.

(Fifth Embodiment)

Figure 15:
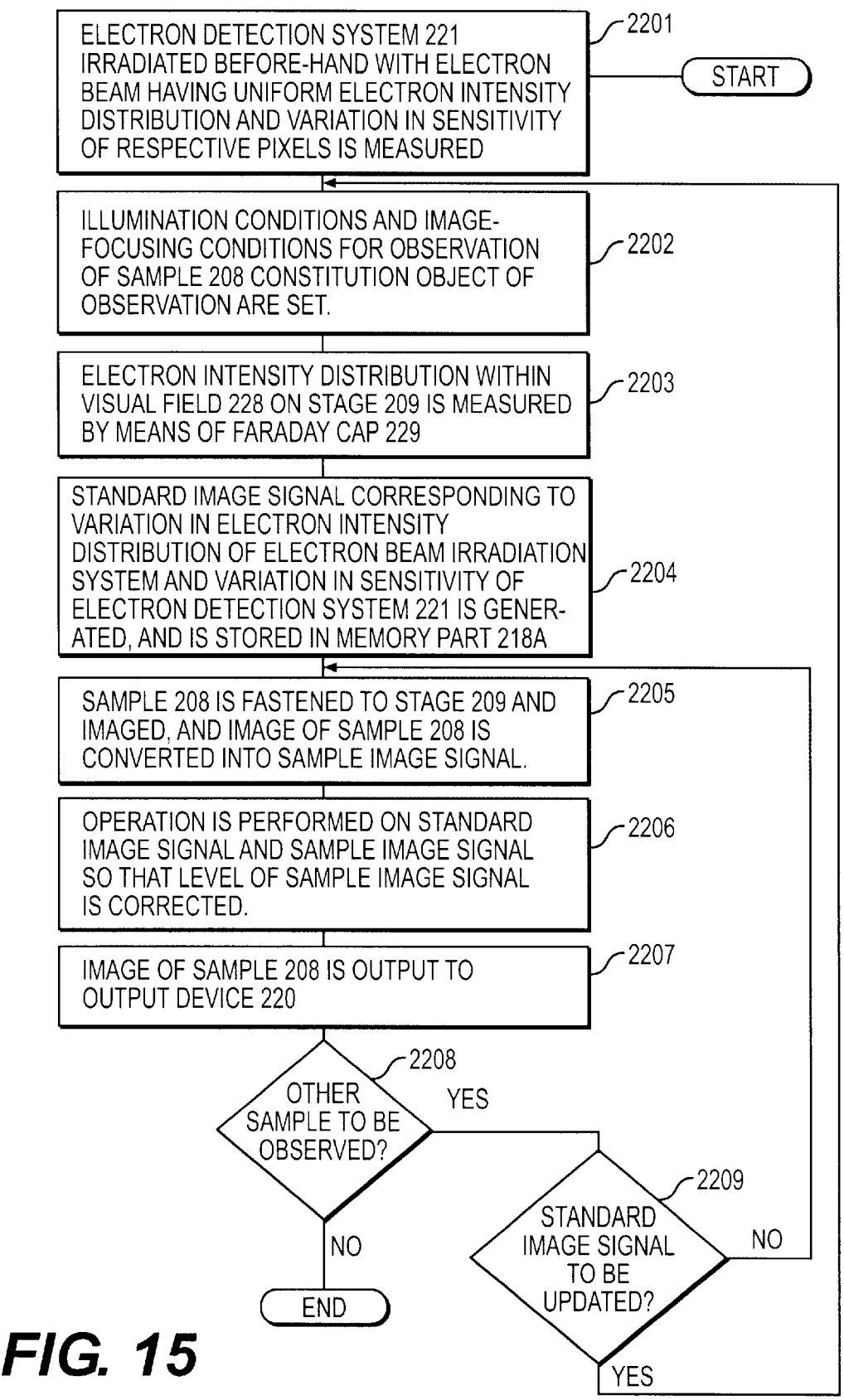
FIG. 15 is a flow chart which illustrates one example of the operation that is performed when a sample is observed using the imaging electron microscope of the fifth embodiment of the present invention.

Next, a fifth embodiment of the present invention will be described with reference to FIGS. 12, 13 and 15. The imaging electron microscope of the present example is equipped with a measurement mechanism that measures the intensity distribution G(x) of the electron beam within the visual field 228 and the detection sensitivity distribution D(x) of the electron detection system 221 for the imaging electron microscope shown in the fourth embodiment. In FIGS. 12 and 13, parts corresponding to FIG. 6 are labeled with the same symbols, and a detailed description of these parts is omitted.

Figure 12A:
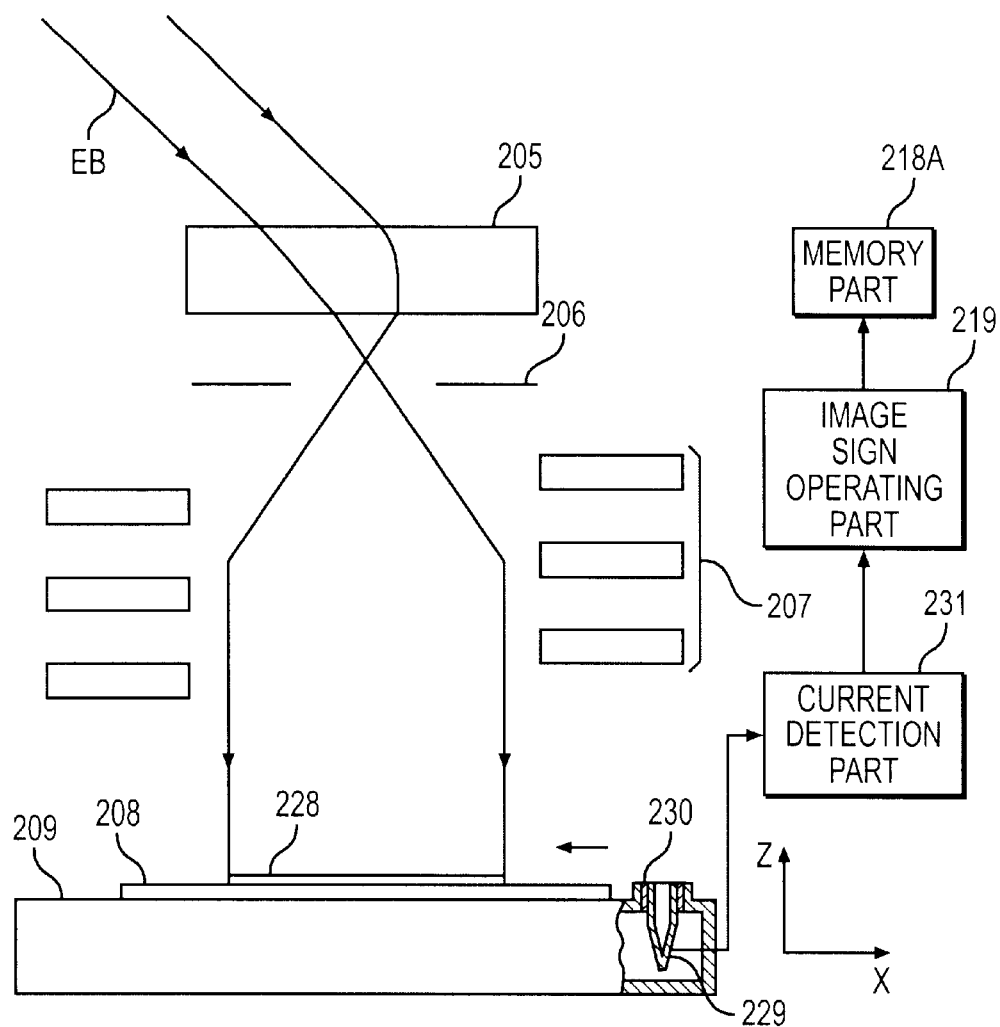
FIG. 12(a) is a partially cut-away structural diagram which illustrates the essential parts of an imaging electron microscope constituting a fifth embodiment of the present invention.

FIG. 12(a) shows an enlarged view of the lower portion of the imaging electron microscope of the present example. In this FIG. 12(a), a Faraday cap 229 which is used to measure the intensity distribution G(x) of the electron beam is installed via an insulator 230 in the vicinity of the sample 208 on the XY stage 209. The detection signal of the Faraday cap 229 used as an intensity distribution measurement system is sent to the image signal operating part 219 via a current detection part 231. The X and Y coordinates of the XY stage 209 measured by means of the laser interferometer 226 shown in FIG. 6 are also sent to the image signal operating part 219.

The Faraday cap 229 is subjected to the irradiation of the electron beam EB, and measures the intensity (current) of this electron beam. When the intensity distribution G(x) is to be measured, the XY stage 209 is driven so that the Faraday cap 229 is moved to the end portion of the visual field 228; then, the Faraday cap 229 is caused to scan in the X direction so that it cuts across the visual field 228 in the X direction, and the current thus obtained is stored as a function of the position x in the X direction. Furthermore, since the resolution (width in the X direction) of the Faraday cap 229 is larger (coarser) than the resolution (width of the respective pixels) of the electron detection system 221, it is desirable that an appropriate interpolation for the position x be performed for the intensity distribution G(x) measured by the Faraday cap 229.

Figure 13A:
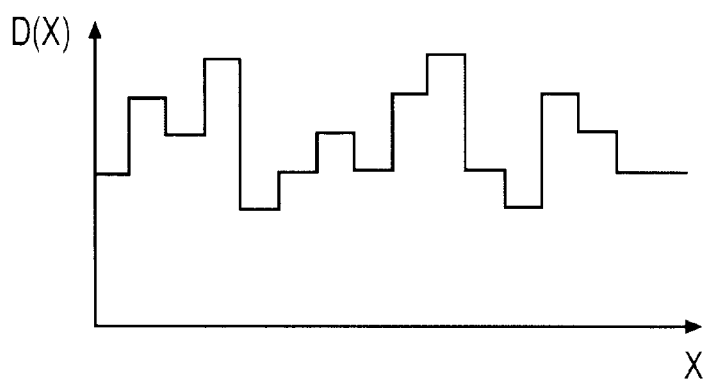
FIG. 13(a) is a graph which illustrates one example of the detection sensitivity distribution $D(x)$ of the electron detection system.
Figure 13B:
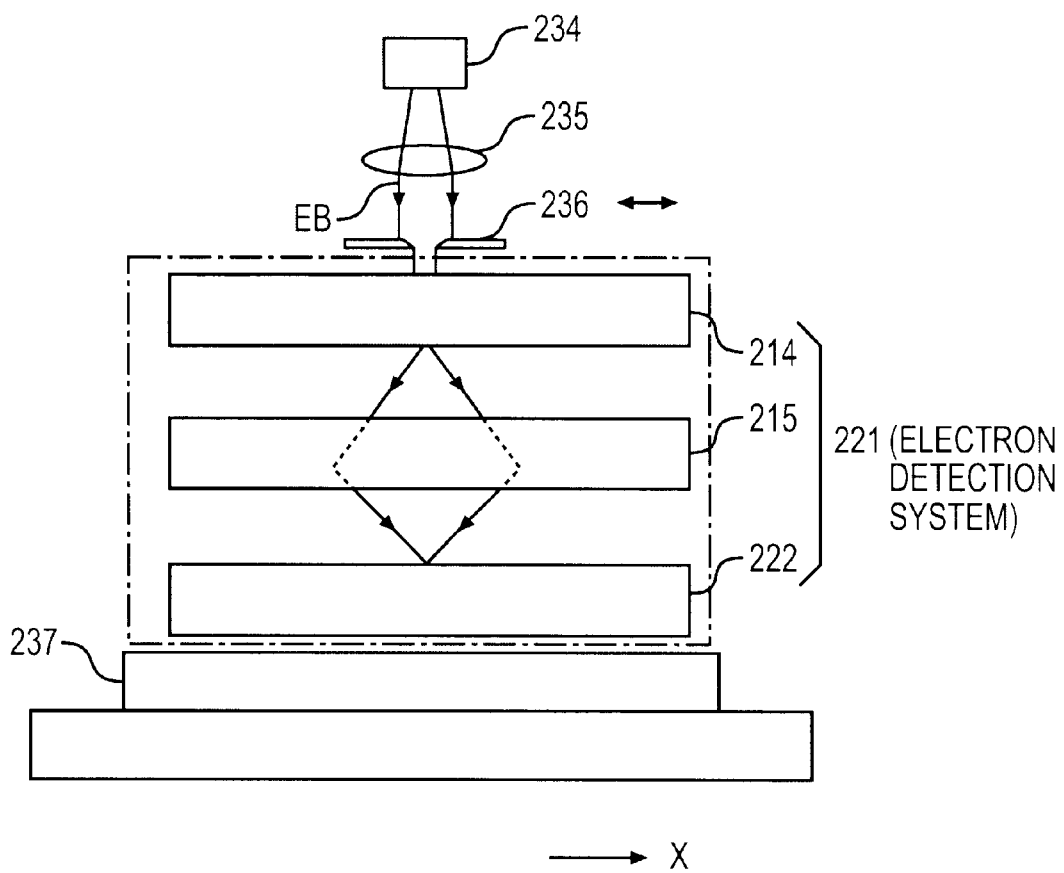
FIG. 13(b) is a diagram which illustrates one example of the mechanism used to measure the detection sensitivity distribution of the electron detection system.

Next, a method of observation using the imaging electron microscope of the present example will be described with reference to the flow chart shown in FIG. 15. First, in step 2201, before the electron detection system 221 is installed in the imaging electron microscope of the present example, the detection sensitivity distribution D(x) of the electron detection system 221 is measured beforehand. FIG. 13(b) shows the conditions of measurement of the detection sensitivity distribution D(x) in the present example; in this FIG. 13(b), the electron detection system 221 is mounted on a stage 237 that can move continuously in the X direction.

Furthermore, when the detection sensitivity distribution D(x) of the electron detection system 221 is measured, the stage 237 is driven so that the electron detection system 221 is caused to scan in the X direction; at the same time, the irradiation surface of the MCP 214 is irradiated with an electron beam EB from an electron beam irradiation device 234 (including an electron gun) via an illumination lens 235 (consisting of an electromagnetic lens) and an aperture plate 236, and after the scanning of the electron detection system 221 is completed, the image signals read out from the TDI sensor 222 are output to the image signal operating part 219 via the image signal processing part 217 shown in FIG. 6. As is shown in FIG. 13(a), the image signal operating part 219 stores the image signals in the memory part 218A as a function D(x) of the position corresponding to the position x in the X direction on the visual field 228. This function D(x) constitutes the detection sensitivity distribution. As a result, an effect similar to that obtained in the case of irradiation with an electron beam having a substantially uniform intensity distribution is realized, so that the detection sensitivity distribution D(x) of the electron detection system 221 can be accurately measured.

Figure 12B:
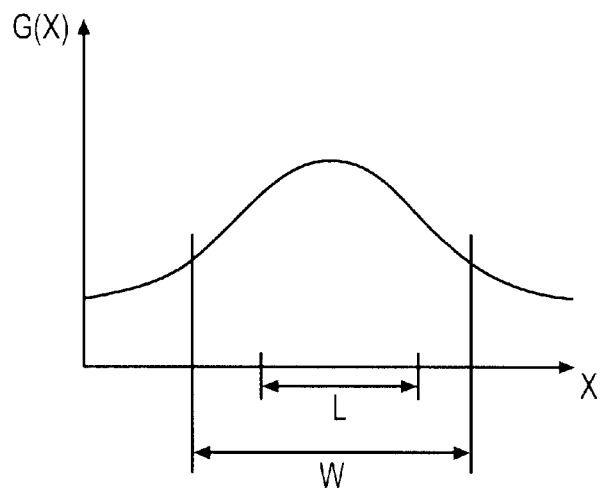
FIG. 12(b) is a graph which illustrates one example of the electron beam intensity distribution $G(x)$ within the visual field 228 measured by means of the Faraday cap 229 shown in FIG. 12(a).

Next, proceeding to step 2202, the image-focusing conditions and illumination conditions for the observation of the sample 208 are set in the same manner as in the fourth embodiment. Then, proceeding to step 2203, the intensity distribution of the electron beam within the visual field 228 is measured while the XY stage 209 is moved so that the Faraday cap 229 is caused to scan in the X direction as shown in FIG. 12(a). Specifically, the image signal operating part 219 stores the current values detected via the Faraday cap 229 in the memory part 218A as a function G(x) of the position x in the X direction within the visual field 228 as shown in FIG. 12(b). This function G(x) is the intensity distribution of the incident electron beam. Then, in step 2204, the image signal operating part 219 determines the product of the intensity distribution G(x) of the electron beam for the visual field 228 and the detection sensitivity distribution D(x) of the electron detection system 221 measured in step 2201, and stores this product G(x)·D(x) in the memory part 218A as a standard image signal.

Next, in step 2205, as in the fourth embodiment, the sample 208 constituting the object of observation is placed on the XY stage 209 and scanned relative to the visual field 228, and images of the sample 208 are converted into sample image signals Im(x). Then, in step 2206, the sample image signals Im(x) are divided by the standard image signals G(x)·D(x), so that quotient signals S'(x) are determined, thus correcting the signal level of the sample image signals Im(x). Since the sample image signals Im(x) can be expressed by the above-mentioned Equation (2), the quotient signals S'(x) constitute the true sample image signals I(x). Accordingly, sample image signals can be obtained in which the effects of variation in the intensity distribution G(x) of the electron beam within the visual field 228 and variation in the detection sensitivity distribution D(x) of the electron detection system 221 are eliminated.

Then, in step 2207, the quotient signals S'(x) whose signal levels have been corrected are (for example) binarized at a prescribed threshold value and output to the output device 220. As a result, defective areas, etc., are displayed. Then, when another sample is to be observed under the same conditions, the processing returns to step 2205 via steps 2208 and 2209, and this other sample is placed on the XY stage 209. Meanwhile, in cases where the standard image signals are to be updated, the processing returns to step 2202 from step 2209, and the illumination conditions and image-focusing conditions for observation are reset, after which the intensity distribution of the electron beam within the visual field 228 is measured.

Thus, in the present example, the intensity distribution G(x) of the electron beam within the visual field 228 and the detection sensitivity distribution D(x) of the electron detection system 221 can be directly measured with a high degree of precision; accordingly, the actual condition of the circuit patterns of the sample 208 can be observed with high precision by correcting these distributions. Furthermore, since the intensity distribution G(x) is measured with a high degree of precision, a region with a greater width of W can be used as the visual field 228 in FIG. 12(b), instead of just the region with a width of L in the center, which has a relatively flat intensity distribution. Accordingly, the measurement efficiency can be further improved.

Thus, in the imaging type observation method of the present embodiment, the effects of the intensity distribution of the charged-particle beam within the visual field can be reduced, so that samples can be accurately observed.

Furthermore, in the above-mentioned working configuration, an electron beam was used as the charged-particle beam; however, the present invention can also be applied in cases where an ion beam, etc., is used as the charged-particle beam.

Thus, the present invention is not limited to the above working configuration; various constructions may be adopted within limits that do not involve any departure from the spirit of the present invention.

What is claimed is:

1. An electron-optical system, comprising:

irradiation means which irradiates a surface of a sample with an irradiating electron beam;

observation means which focuses an observational electron beam emitted from the surface of the sample as an image on electron beam detection means, the observation means including a cathode lens; and an accelerating electric field is formed by the surface of the sample and the cathode lens, the surface of the sample is biased to a negative potential (−V1, V1>0), the cathode lens has a plurality of electrodes, at least one of said plurality of electrodes is biased to a positive potential (V2, V2>V1), so that the observational electron beam that has just been emitted from the surface of the sample is accelerated monotonically, without a decrease in velocity, to the energy of approximately (V1+V2).

2. An electron-optical system, comprising:

an irradiating beam source;

an irradiation optical system which causes an irradiating electron beam emitted from the irradiating beam source to be incident on a beam separator;

an objective optical system which causes an irradiating electron beam that passes through the beam separator to be incident on a surface of a sample, the observation means including a cathode lens;

an image-focusing optical system which causes an observational electron beam that is emitted from the surface of the sample, and that passes through the beam separator in a direction that is different from the direction leading to the irradiating beam source, to be incident on electron beam detection means; and an accelerating electric field is formed by the surface of the sample and the cathode lens, the surface of the sample is biased to a negative potential (−V1, V1>0), the cathode lens has a plurality of electrodes, at least one of said plurality of electrodes is biased to a positive potential (V2, V2>V1), so that the observational electron beam that has just been emitted from the surface of the sample is accelerated monotonically, without a decrease in velocity, to the energy of approximately (V1+V2).

3. The electron-optical system according to claim 2, wherein the beam separator is a Wien filter, the irradiating electron beam is bent by the Wien filter, and the observational electron beam passes through the Wien filter without being bent.

4. The electron-optical system according to claim 2, wherein the electron beam detection means comprises a TDI sensor.

5. The electron-optical system according to claim 3, wherein the electron beam detection means comprises a TDI sensor.

6. An inspection method using an electron-optical system, comprising steps of:

guiding an irradiating electron beam emitted from an irradiating beam source via an irradiation optical system so as to be incident on a beam separator;

guiding the irradiating electron beam that has passed through the beam separator via an objective optical system so as to be incident on a surface of a sample and so as to emit an observational electron beam from the surface of the sample;

guiding the observational electron beam via the objective optical system so as to be incident on the beam separator;

guiding the observational electron beam via the beam separator in a direction that is different from the direction leading to the irradiating beam source; and guiding the observational electron beam that has passed through the beam separator via an image-focusing optical system so as to be incident on electron beam detection means, wherein the objective optical system includes a cathode lens, an accelerating electric field is formed by the surface of the sample and the cathode lens, and the surface of the sample is biased to a negative potential (−V1, V1>0), the cathode lens has a plurality of electrodes, at least one of said plurality of electrodes is biased to a positive potential (V2, V2>V1), so that the observational electron beam that has just been emitted from the surface of the sample is accelerated monotonically, without a decrease in velocity, to the energy of approximately (V1+V2).

7. The inspection method according to claim 6, wherein the beam separator is a Wien filter, the irradiating electron beam is bent by the Wien filter, and the observational electron beam passes through the Wien filter without being bent.

8. The inspection method according to claim 6, wherein the electron beam detection means comprises a TDI sensor.

9. The inspection method claimed according to claim 7, wherein the electron beam detection means comprises a TDI sensor.

10. The electron-optical system according to claim 1, wherein the observational electron beam that has been accelerated to the energy of approximately (V1+V2) is reduced to the energy of V1 (ground potential) by another of the plurality of electrodes which is ground potential.

11. The electron-optical system according to claim 2, wherein the observational electron beam that has been accelerated to the energy of approximately (V1+V2) is reduced to the energy of V1 (ground potential) by another of the plurality of electrodes which is ground potential.

12. The electron-optical system according to claim 6, wherein the observational electron beam that has been accelerated to the energy of approximately (V1+V2) is reduced to the energy of V1 (ground potential) by another of the plurality of electrodes which is ground potential.

* * * * *